US006826428B1

(12) United States Patent
Chen et al.

(10) Patent No.: US 6,826,428 B1
(45) Date of Patent: Nov. 30, 2004

(54) GASTROINTESTINAL ELECTRICAL STIMULATION

(75) Inventors: Jiande Chen, Houston, TX (US); Pankaj Jay Pasricha, Houston, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 117 days.

(21) Appl. No.: 09/913,556

(22) PCT Filed: Oct. 11, 2000

(86) PCT No.: PCT/US00/28128
§ 371 (c)(1),
(2), (4) Date: Mar. 27, 2002

(87) PCT Pub. No.: WO01/76690
PCT Pub. Date: Oct. 18, 2001

Related U.S. Application Data
(60) Provisional application No. 60/195,977, filed on Apr. 11, 2000.

(51) Int. Cl.⁷ ............................................... A61N 1/18
(52) U.S. Cl. ..................................................... 607/40
(58) Field of Search ................... 607/40, 41, 138, 607/133

(56) References Cited

U.S. PATENT DOCUMENTS

| | | | |
|---|---|---|---|
| 3,909,883 A | | 10/1975 | Fegen |
| 5,188,104 A | | 2/1993 | Wernicke et al. |
| 5,197,491 A | | 3/1993 | Anderson et al. |
| 5,263,480 A | | 11/1993 | Wernicke et al. |
| 5,423,872 A | | 6/1995 | Cigaina |
| 5,540,730 A | * | 7/1996 | Terry et al. .................... 607/40 |
| 5,556,425 A | | 9/1996 | Hewson et al. |
| 5,649,902 A | | 7/1997 | Yoon |
| 5,690,691 A | | 11/1997 | Chen et al. |
| 5,716,392 A | | 2/1998 | Bourgeois et al. |
| 5,836,994 A | | 11/1998 | Bourgeois |
| 5,861,014 A | | 1/1999 | Familoni |
| 5,882,340 A | | 3/1999 | Yoon |
| 5,935,126 A | | 8/1999 | Riza |
| 5,995,872 A | | 11/1999 | Bourgeois |
| 6,026,326 A | | 2/2000 | Bardy |
| 6,051,017 A | | 4/2000 | Loeb et al. |
| 6,571,127 B1 | * | 5/2003 | Ben-Haim et al. ............ 607/40 |

FOREIGN PATENT DOCUMENTS

| | | |
|---|---|---|
| WO | WO/99/03532 | 1/1999 |
| WO | WO/99/30776 | 6/1999 |

OTHER PUBLICATIONS

Bellahsene et al., IEEE/Ninth Annual Conf. of Eng. in Med. and Biol. Soc. (1987).
Bellahsene et al, American Physiology Society, (1992).
Jiande Chen, Identifying No. 1R43DK55437–01 (1999).
Jiande Chen, Identifying No. 121442 (1998).
Chen et al., J. Gastroenterology & Hepatology, 13:S232–236(Suppl)(1998).
Chen et al., IEEE–EMBC & CMBEC :1691–1692(1995).
Kuwahara, Jap. J. Phys., 33:29–40(1983).
Lin et al., AJP–Gastrointestinal & Liver Physiology, 274(1):G186(1998).
Lin et al., Am. J. Gastroenterology, 92(9):1527–1530(1997).
McCallum et al., Gastroenterology, 114:456–461(1998).
Mintchev et al., Gastroenterology, 118:258–263(2000).
Mintchev et al., Annals of Biomedical Engineering, 25:726–730(1997).
Mintchev et al., Gut, 43:607–611(1998).
Mintchev et al., J. Med. Eng. (1999).

* cited by examiner

*Primary Examiner*—Jeffrey R. Jastrzab
(74) *Attorney, Agent, or Firm*—Rogalskyj & Weyand, LLP

(57) ABSTRACT

The present invention is directed to a method of regulating gastrointestinal action in a subject using a stimulatory electrode and a sensor to provide retrograde feedback control of electrical stimulation to the GI tract. The invention is further directed to a method for reducing weight in a subject, again using a stimulatory electrode and a sensor to provide retrograde feedback control of electrical stimulation to the stomach. The invention is further directed to a method of providing electrical field stimulation to a gastrointestinal organ, as well as a method of providing an electrical potential gradient in a gastrointestinal organ. Further provided is a method of stimulating the vagus nerve of a subject. Additionally provided is a method of placing a device in the gastrointestinal tract or wall of a subject from the exterior of the subject, using a needle to insert the device.

11 Claims, 11 Drawing Sheets

☐ session1  ■ session2  ☐ session3

☐ session1  ■ session2  ☐ session3

Baseline      Gastric Stimulation

GASTROINTESTINAL ELECTRICAL STIMULATION

This application claims priority of U.S. Provisional Patent Application Ser. No. 60/195,977, filed Apr. 11, 2000.

FIELD OF THE INVENTION

The present invention relates generally to gastrointestinal electrical stimulation, and more particularly to methods for regulating gastrointestinal action, reducing weight, providing electrical field stimulation to a gastrointestinal organ, providing electrical potential gradient in a gastrointestinal organ, stimulating the vagus nerve, and placing a device in the gastrointestinal tract or wall.

BACKGROUND OF THE INVENTION

Throughout this application various publications are referenced, many in parenthesis. Full citations for each of these publications are provided at the end of the Detailed Description and throughout the Detailed Description. The disclosures of each of these publications in their entireties are hereby incorporated by reference in this application.

Motility is one of the most critical physiological functions of the human gut. Without coordinated motility, digestion and absorption of dietary nutrients could not take place. To accomplish its functions effectively, the gut needs to generate not just simple contractions but contractions that are coordinated to produce transit of luminal contents (peristalsis). Thus, coordinated gastric contractions are necessary for the emptying of the stomach. The patterns of gastric motility are different in the fed state and the fasting state (Yamada et al. 1995). In the fed state, the stomach contracts at its maximum frequency, 3 cycles/min (cpm) in humans and 5 cpm in dogs. The contraction originates in the proximal stomach and propagates distally toward the pylorus. In healthy humans, the ingested food is usually emptied by 50% or more at 2 hours after the meal and by 95% or more at 4 hours after the meal (Tougas et al. 2000). When the stomach is emptied the pattern of gastric motility changes. The gastric motility pattern in the fasting state undergoes a cycle of periodic fluctuation divided into three phases: phase I (no contractions, 40–60 minutes), phase II (intermittent contractions, 20–40 minutes) and phase III (regular rhythmic contractions, 2–10 minutes).

Gastric motility (contractile activity) is in turn regulated by myoelectrical activity of the stomach. Gastric myoelectrical activity consists of two components, slow waves and spike potentials (Chen and McCallum 1995). The slow wave is omnipresent and occurs at regular intervals whether or not the stomach contracts. It originates in the proximal stomach and propagates distally toward the pylorus. The gastric slow wave determines the maximum frequency, propagation velocity and propagation direction of gastric contractions. When a spike potential (similar to an action potential), is superimposed on the gastric slow wave a strong lumen-occluded contraction occurs. The normal frequency of the gastric slow wave is about 3 cpm in humans and 5 cpm in dogs. A noninvasive method similar to electrocardiography, called electrogastrography, has been developed and applied to detect gastric slow waves using abdominal surface electrodes (Chen and McCallum 1995).

Abnormalities in gastric slow waves lead to gastric motor disorders and have been frequently observed in patients with functional disorders of the gut, such as gastroparesis, functional dyspepsia, anorexia and etc. (Chen and McCallum 1995). Gastric myoelectrical abnormalities include uncoupling and gastric dysrhythmia and can lead to significant impairment in gastric emptying (Lin et al. 1998; Chen et al. 1995a; Telander et al. 1978; You and Chey 1985; Chen and McCallum 1993). Tachygastria (an abnormally high frequency of the gastric slow wave) is known to cause gastric hypomotility (Lin et al. 1998; Chen et al. 1995a; Telander et al. 1978; You and Chey 1985; Chen and McCallum 1993).

Gastric emptying plays an important role in regulating food intake. Several studies have shown that gastric distention acts as a satiety signal to inhibit food intake (Phillips and Powley 1996) and rapid gastric emptying is closely related to overeating and obesity (Duggan and Booth 1986). In a study of 77 subjects composed of 46 obese and 31 age-, sex-, and race-matched nonobese individuals, obese subjects were found to have a more rapid emptying rate than nonobese subjects (Wright et al. 1983). Obese men were found to empty much more rapidly than their nonobese counterparts. It was concluded that the rate of solid gastric emptying in the obese subjects is abnormally rapid. Although the significance and cause of this change in gastric emptying remains to be definitively established, it has been shown that several peptides, including cholecystokinin (CCK) and corticotropin-releasing factor (CRF), suppress feeding and decrease gastric transit. The inhibitory effect of peripherally administered CCK-8 on the rate of gastric emptying contributes to its ability to inhibit food intake in various species (Moran and McHugh 1982). CRF is also known to decrease food intake and the rate of gastric emptying by peripheral injection (Sheldon et al. 1990). More recently, it was shown that in ob/ob mice (a genetic model of obesity), the rate of gastric emptying was accelerated compared with that in lean mice (Asakawa et al. 1999). Urocortin, a 40-amino acid peptide member of the CRF family, dose-dependently and potently decreased food intake and body weight gain as well as the rate of gastric emptying, in ob/ob mice. This suggests that rapid gastric emptying may contribute to hyperphagia and obesity in ob/ob mice and opens new possibilities for the treatment of obesity.

There have been a number of reports on gastrointestinal electrical stimulation for the treatment of gastrointestinal motility disorders in both dogs and humans (U.S. Pat. Nos. 5,423,872, 5,690,691, and 5,836,994; PCT International Publication No. WO 99/30776; Bellahsene et al. 1992; Mintchev et al. 1998; Mintchev et al. 1999; Mintchev et al. 2000; Chen et al. 1998; Chen et al. 1995c). These disorders are characterized by poor contractility and delayed emptying (by contrast with obesity) and the aim of electrical stimulation in this setting is to normalize the underlying electrical rhythm and improve these parameters. In general, this is done by antegrade or forward gastric (or intestinal) stimulation.

Previous work on antegrade gastrointestinal stimulation has been focused on its effects on a) gastric myoelectrical activity, b) gastric motility, c) gastric emptying, and d) gastrointestinal symptoms (Lin et al. 1998; Eagon and Kelly 1993; Hocking et al. 1992; Lin et al. 2000a; McCallum et al. 1998; Miedema et al. 1992; Qian et al. 1999; Abo et al. 2000; Bellahsene et al. 1992). These studies have conclusively shown that entrainment of gastric slow waves is possible using an artificial pacemaker. Recent studies have indicated that such entrainment is dependent on certain critical parameters, including the width and frequency of the stimulation pulse (Lin et al. 1998). It has also been shown that antegrade intestinal electrical stimulation can entrain intestinal slow waves using either serosal electrodes (Lin et al. 2000a) or intraluminal ring electrodes (Bellahsene et al. 1992).

Obesity is one of the most prevalent public health problems in the United States. According to the National Health and Nutrition Examination Survey, "overweight" (body mass index or BMI=25.0–29.9 kg/m$^2$) adults now represent 59.4% of the male and 50.7% of the female population in this country, totaling more than 97 million people. The corresponding figures for "obesity" (BMI≧30) are about 19.5% for men and 25% for women, involving a total of almost 40 million people. "Morbid obesity" or clinically severe obesity (BMI≧40 or >100 lbs over normal weight) affects more than 15 million Americans (Kuczmarski et al. 1994; Troiano et al. 1995; Flegal et al. 1998; Kuczmarski et al. 1997). The treatment of obesity and its primary comorbidities costs the US healthcare system more than $100 billion each year (Klein 2000; Martin et al. 1995; Colditz 1992; Wolf and Colditz 1998); in addition, consumers spend in excess of $33 billion annually on weight-reduction products and services (House Committee 1990). Moreover, obesity is associated with an increased prevalence of socioeconomic hardship due to a higher rate of disability, early retirement, and widespread discrimination (Enzi 1994; Gortmaker et al. 1993).

Obesity is a complex, multifactorial and chronic condition characterized by excess body fat. Obesity results from an imbalance between energy expenditure and caloric intake. Although the causes of this imbalance are not completely understood, genetic and/or acquired physiologic events and environmental factors are important. Recent studies have shown that approximately a third of the variance in adult body weights results from genetic influences (Stunkard 1996). In this regard, much attention has been paid to leptin, an adipocyte- and placenta-derived circulating protein that communicates the magnitude of fat stores to the brain. A deficiency of leptin (ob/ob) or a defective leptin receptor (db/db) seems responsible for obesity in ob/ob and db/db mice and obese Zucker rats (Frederich et al. 1995). Various gastrointestinal peptides, such as cholecystokinin, enterostatin and glucagon and neurotransmitters (serotonin) that provide communication between the brain, gastrointestinal tract and adipose tissue also may have an etiologic role in obesity (Bandini et al. 1990). Possible environmental mechanisms for obesity involve pharmacologic agents (such as antipsychotic drugs and certain antidepressants), cultural and ethnic factors (Morley 1987), hyperphagia and high fat intake (Sobal and Stunkard 1989), inactivity, and psychological factors, such as overeating resulting from emotional distress, including poor mood or depression and low self-esteem (Namnoum 1993).

Obesity is a major risk factor for many chronic diseases, including diabetes mellitus type II, cardiovascular diseases, reproductive disorders, certain cancers, gallbladder disease, respiratory disease and other comorbidities, such as osteoarthritis, edema, gastroesophageal reflux, urinary stress incontinence, idiopathic intracranial hypertension, or venous stasis disease of the lower extremities (AACE/ACE Position 1998). Although patients with type II diabetes are not necessarily obese, weight gain before the development of type II diabetes is common (Despres 1993). Obesity is the most powerful environmental risk factor for diabetes mellitus type II (Kissebah et al. 1989) and the prevalence of diabetes is 2.9 times higher in overweight (BMI ≧27.8 in men and ≧27.3 in women) than in non-overweight subjects 20 to 75 years of age (NIH 1985). When this age range is narrowed to between 20 and 45 years, this risk is 3.8 times higher (Van Itallie 1985). Mortality due to cardiovascular disease is almost 50% higher in obese patients than in those of average weight and is 90% higher in those with severe obesity (Namnoum 1993). Sixty percent of obese patients have hypertension (Alpert and Hashimi 1993). Fatty infiltration of the myocardium, right hypertrophy, excess epicardial fat, abnormalities of ventricular function, and increased left ventricular filling pressure all seem closely related to the duration of obesity (Nakajima et al. 1985). Obesity has a detrimental effect on female reproductive function (Thompson 1997). In comparison with normal-weight women, obese female patients have a higher mortality rate from cancer of the gallbladder, biliary passages, breast, uterus and ovaries (NIH 1985). Obese men have a higher rate of mortality from rectal and prostate cancer than nonobese men (NIH 1985). Both obese men and women have an increased risk of colon cancer. Obesity is a common cause of sleep apnea and about 50% to 70% of patients diagnosed with sleep apnea are obese (Douglas 1995). Sleep apnea is associated with an increased risk of vehicular accidents and cardiovascular and cerebrovascular incidents (Douglas 1995).

In the past, the success of treatment modalities for obesity was measured by the rate and amount of weight loss. More recently, success is being measured by the ability to achieve and maintain a clinically helpful and significant weight loss and by the salutary effects of weight loss on comorbidities of obesity. The treatment of obesity can be classified into three categories: general measures, pharmacotherapy and surgical treatment.

Typically, an obese patient is first counseled about adopting some general measures such as caloric restriction, behavior therapy and physical activity. The goal of this program is to integrate positive eating and physical activity behaviors into the patient's life. Although an acceptable weight loss may be achieved with such measures, maintaining weight loss seems to be more difficult, particularly for patients who were treated with caloric restriction. About 50% of patients regain weight within one year after the treatment and almost all patients regain weight within 5 years (AACE/ACE Position 1998).

Pharmacotherapy of obesity has been problematic. Amphetamine derivatives such as fenfluramine and dexfenfluramine have been commonly used until their recent withdrawal from the market due to the long-term risk of cardiovascular effects (Bray and Greenway 1999). A number of other FDA-approved drugs are currently available for the medical treatment of obesity. These include sibutramine, diethylpropion, mazindol, phentermine, phenylpropanolamine, orlistat etc. (Bray and Greenway 1999; Hvizdos et al. 1999). Sibutramine, a centrally acting antiobesity agent, was recently approved by the FDA for use up to 1 year. Its clinical efficacy has been evaluated in about 4,600 patients worldwide (Smith 1997). Its adverse events include dry mouth, anorexia and constipation. It has several drug interactions and cannot be used in patients with poorly controlled or uncontrolled hypertension, severe renal impairment, severe hepatic dysfunction, congestive heart failure, coronary artery disease, and etc. Diethylpropion, mazindol and phentermine are approved only for short-term use and their clinical efficacy is very much limited. Diethlpropion, an anorexic agent, is effective in producing weight loss but is indicated for use up to only a few weeks. A clinical trial indicated a weigh loss ranging from 6.6 kg to 11.3 kg but 82% of the 200 patients did not complete the trial (Le Riche and Csima 1967). Mazindol, structurally related to the tricyclic antidepressant agents, seems to act by blocking norepinephrine reuptake and synaptically release dopamine. It is effective as an appetite suppressant. Loss of weight of 12 to 14 kg was reported in a one-year study.

However, the placebo group also showed a weight loss of 10 kg (Enzi et al. 1976). Phenylpropanolamine is an over-the-counter drug as an aid in weight reduction. This agent acts on the $\alpha_1$-receptor and is used systemically as an appetite suppressant. In a comprehensive obesity-management program, it was shown an increased weight loss by 0.25 to 0.5 pound weekly in comparison with placebo. However, its effect diminishes after 4 weeks (Lasagna 1988; Greenway 1992).

Surgical treatment is typically reserved for patients with morbid obesity (BMI>40) (Consensus Development 1991). Two options are generally available. The first is a restrictive operation designed to make the stomach smaller, such as vertical banded gastroplasty (also called gastric stapling) which can be done laparoscopically (Doldi et al. 2000; Balsiger et al. 2000). Vertical banded gastroplasty results in a weight loss for at least 2 years (Sagar 1995) but some of the weight lost may be regained within 5 years (Nightengale et al. 1991). Longer follow-up studies are not available (Sagar 1995). The second kind of surgery is a gastric bypass operation that promotes mal-digestion of ingested nutrients. This includes procedures such as Roux-en-Y gastric bypass or extensive gastric bypass (biliopancreatic diversion) (Institute of Medicine 1995; Benotti and Forse 1995; Fried and Peskova 1997; Scorpinaro et al. 1996; Scopinaro et al. 1981). Roux-en Y gastric bypass produces more substantial weight loss than vertical banded gastroplasty (Brolin et al. 1992; Sugerman et al. 1992). This procedure is a more complicated gastric bypass that successfully promotes weight loss. Other surgical approaches include intestinal bypass (effective but associated with major complications), jaw wiring (effective while used), and liposuction (cosmetic procedure). The risks involved with surgical treatment of morbid obesity are substantial. While the immediate operative mortality rate for both vertical banded gastroplasty and Roux-en-Y gastric bypass has been relative low, morbidity in the early postoperative period (wound infections, dehiscence, leaks from staple-line breakdown, stomal stenosis, marginal ulcers, various pulmonary problems and deep thrombophlebitis in the aggregate) may be as high as 10% or more. In the later postoperative period, other problems may arise and may require reoperative surgery. Such problems include pouch and distal esophageal dilation, persistent vomiting (with or without stomal obstruction), cholecystitis or failure to lose weight. Moreover, mortality and mobidity associated with reoperative surgery are higher than those associated with primary operations. In the long term, micronutrient deficiencies, particularly of vitamin $B_{12}$, folate and iron, are common after gastric bypass and must be sought and treated. Another potential result of this operation is the so-called "dumping syndrome" which is characterized by gastrointestinal distress and other symptoms.

A need continues to exist for additional feasible and suitable means to treat obesity. Likewise, a need continues to exist for additional feasible and suitable means to treat other gastrointestinal tract disorders.

SUMMARY OF THE INVENTION

To this end, the subject invention provides a method of regulating gastrointestinal action in a subject. The method comprises determining an optimum level of total gastrointestinal action in a subject, the total gastrointestinal action including naturally occurring gastrointestinal action and non-naturally occurring gastrointestinal action; positioning a stimulatory electrode relative to the subject so that the stimulatory electrode can generate non-naturally occurring gastrointestinal action; positioning a sensor relative to the subject so that the sensor senses the level of total gastrointestinal action, the sensor being operatively connected to the stimulatory electrode; periodically detecting the level of total gastrointestinal action with the sensor; and periodically generating non-naturally occurring gastrointestinal action with the stimulatory electrode when the detected level of total gastrointestinal action differs from the optimum level until the detected level of total gastrointestinal action substantially equals the optimum level.

The invention further provides a method for reducing weight in a subject having a stomach. The method comprises determining an optimum level of total stomach electrical activity in a subject which reduces weight in the subject, the total stomach electrical activity including naturally occurring stomach electrical activity and non-naturally occurring stomach electrical activity; positioning a stimulatory electrode relative to the subject so that the stimulatory electrode can generate non-naturally occurring stomach electrical activity; positioning an electrical activity sensor relative to the subject so that the electrical activity sensor senses the level of total stomach electrical activity, the electrical activity sensor being operatively connected to the stimulatory electrode; periodically detecting the level of total stomach electrical activity with the electrical activity sensor; and periodically generating non-naturally occurring stomach electrical activity with the stimulatory electrode when the detected level of total stomach electrical activity differs from the optimum level until the detected level of total stomach electrical activity substantially equals the optimum level.

Also provided is a method of providing electrical field stimulation to a gastrointestinal organ. The method comprises positioning a first stimulatory electrode in a gastrointestinal organ; positioning a second stimulatory electrode in the gastrointestinal organ, the second stimulatory electrode being positioned at least about two centimeters from the first stimulatory electrode; and electrically stimulating the gastrointestinal organ simultaneously through the first and the second stimulatory electrodes, wherein one of the first and the second stimulatory electrodes has a positive polarity and wherein the other one of the first and the second stimulatory electrodes has a negative polarity, thereby providing electrical field stimulation to the gastrointestinal organ between the first and the second stimulatory electrodes.

Additionally provided is a method of providing electrical potential gradient in a gastrointestinal organ. The method comprises positioning a first stimulatory electrode in a gastrointestinal organ; positioning a second stimulatory electrode in the gastrointestinal organ, the second stimulatory electrode being positioned at least about two centimeters from the first stimulatory electrode; and electrically stimulating the gastrointestinal organ simultaneously through the first and the second stimulatory electrodes, wherein voltage generated by the first stimulatory electrode differs from voltage generated by the second stimulatory electrode, thereby providing an electrical potential gradient in the gastrointestinal organ between the first and the second stimulatory electrodes.

The invention further provides a method of stimulating the vagus nerve of a subject. The method comprises positioning a stimulatory electrode in a gastrointestinal organ of a subject; and generating electrical current in the gastrointestinal organ of the subject with the stimulating electrode, wherein the electrical current in the gastrointestinal organ of the subject stimulates the vagus nerve of the subject.

The invention also provides a method of placing a device in the gastrointestinal tract of a subject from the exterior of the subject. The method comprises inserting an end of a needle having an interior bore from the exterior of a subject into the gastrointestinal tract of the subject, the gastrointestinal tract of the subject having a center defined by a wall, the wall having a thickness defining an interior wall adjacent to the center and an exterior wall, and the end of the needle being inserted through the wall into the center of the gastrointestinal tract; inserting a device through the interior bore of the needle, wherein the device has an interior wall engaging means and wherein the device is inserted at least until the interior wall engaging means extends beyond the interior bore of the needle; removing the needle; and retracting the device until the interior wall engaging means engages the interior wall of the gastrointestinal tract of the subject, thereby placing the device in the gastrointestinal tract of the subject. Alternatively, the invention provides a method of placing a device in the gastrointestinal wall of a subject from the exterior of the subject. This method comprises inserting an end of a needle having an interior bore from the exterior of a subject into the gastrointestinal wall of the subject, the gastrointestinal wall defining a center of a gastrointestinal tract of the subject, the gastrointestinal wall having a thickness defining an interior wall adjacent to the center and an exterior wall, and the needle being inserted until the end of the needle is positioned in the thickness of the wall between the interior wall and the exterior wall; inserting a device through the interior bore of the needle, wherein the device has an engaging means and wherein the device is inserted until the engaging means extends beyond the interior bore of the needle into the thickness of the wall; removing the needle; and retracting the device until the engaging means engages the thickness of the wall, thereby placing the device in the gastrointestinal wall of the subject.

BRIEF DESCRIPTION OF THE DRAWINGS

These and other features and advantages of this invention will be evident from the following detailed description of preferred embodiments when read in conjunction with the accompanying drawings in which.

DETAILED DESCRIPTION OF THE INVENTION

Figure 1:
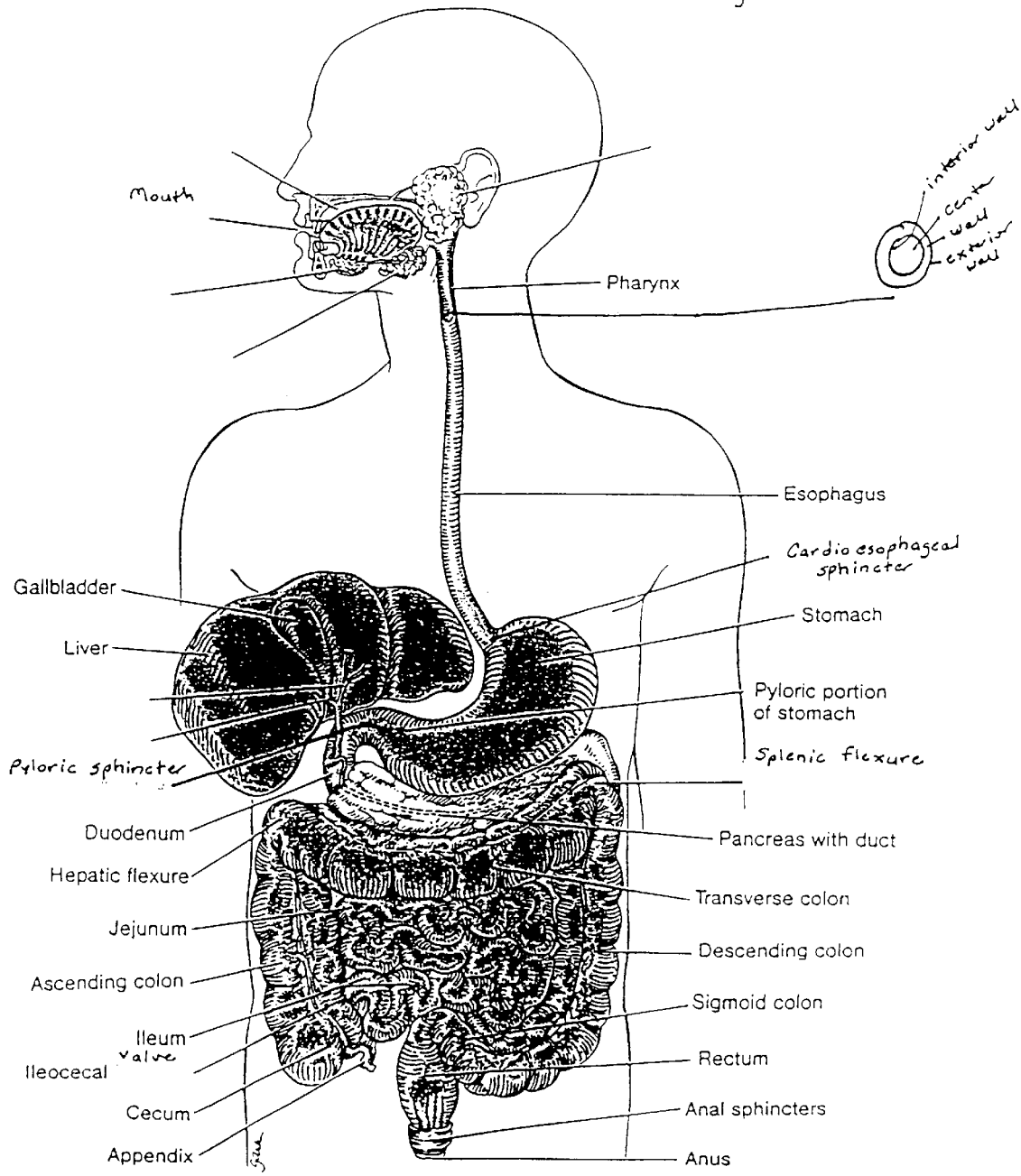
FIG. 1 is a general diagram of the gastrointestinal tract of a human subject.

As used herein, the "gastrointestinal tract" (GI tract) refers to the "gut" or the "alimentary canal" that is a continuous, coiled, hollow, muscular tube that winds through the ventral body cavity (see FIG. 1). It is open to the external environment at both ends. In a human, it's organs (gastrointestinal organs) generally include the mouth, pharynx, esophagus, stomach, small intestine (duodenum, jejunum, and ileum), and large intestine (cecum, appendix, colon, rectum, and anal canal). The large intestine leads to the terminal opening, or anus.

The "gastrointestinal wall" refers to the continuous, coiled, hollow, muscular tube that is the gastrointestinal tract. The wall generally defines the center (lumen) of the GI tract (the hollow portion of the tube). The wall has a thickness defining an interior wall adjacent to the center of the GI tract and an exterior wall (see FIG. 1 insert).

As used herein, "gastrointestinal action" refers to any GI actions which are generated by electrical activity. Thus, gastrointestinal action includes, for example, gastrointestinal electrical activity, gastrointestinal contractile activity (such as stomach contractile activity), gastrointestinal motility, gastric emptying, gastrointestinal pressure, gastrointestinal impedence, and afferent nerve activity (including vagal nerve, sympathetic nerves, and spinal nerves).

A subject refers to an animal, including a human, subject. For non-human animal subjects, the particular structure of the GI tract may differ from that shown in FIG. 1. For such non-human animal subjects, the gastrointestinal tract, as used herein, refers to that non-human animal's known GI tract and GI organs.

An "optimum level" refers to a pre-determined target, which is determined based on the desired outcome. For example, in RGES (see below), the definition of optimization is based on an optimal combination of efficacy, safety and feasibility. That is, the optimal RGES settings are those that result in a significant reduction in food intake (efficacy) but do not induce undesired symptoms, such as nausea or vomiting (safety) with minimal energy (maximally feasible for an implantable device). Iterative adjustments of stimulation parameters are made to achieve this result. For any particular gastrointestinal action, an "optimum level" or desirable level can be determined by monitoring the appropriate GI action. As another example, an appropriate amount of GI pressure at the esophageal sphincter can be determined which prevents reflex of stomach juices into the esophagus, while still allowing the passage of food items into the stomach. With this predetermined "optimum level", a stimulatory electrode can be established with a sensor to maintain this optimum level. The optimum level is thus fact and subject specific, but readily determinable with routine experimentation, taking into account the goal of an optimal combination of efficacy, safety and feasibility.

"Total gastrointestinal action", refers to the sum total of levels of any naturally occurring gastrointestinal action and levels of any non-naturally occurring gastrointestinal action. Naturally occurring gastrointestinal action refers to spontaneous gastrointestinal action that is present in a subject prior to a particular treatment. Non-naturally occurring gastrointestinal action refers to non-spontaneous gastrointestinal action generated by the hand of man or otherwise caused to occur by the particular treatment of the subject. It is important to note that the non-naturally occurring gastrointestinal action which is generated and which is non-spontaneous GI action may in fact be identical (in a physiological sense, for example) to a naturally occurring GI action once it has been generated. For example, a subject may have a naturally occurring level of stomach electrical activity of "X". A stimulatory electrode is positioned to generate a non-naturally occurring level of stomach electrical activity of "Y". The total gastrointestinal action, which is stomach electrical activity in this example, is therefore "X+Y".

A "stimulatory electrode" refers to a conductor of electricity through which current enters a medium (a subject), whereas a "sensor" refers to a conductor of electricity through which current leaves a medium (a subject). Typically, for gastrointestinal uses, the stimulatory electrodes and sensors are constructed of teflon-insulated wires such as are used for cardiac pacing wires. The stimulatory electrode is electrically connected (i.e., conductively connected) to a source of electrical current (often referred to as a pacemaker where a set pattern of electrical current is delivered), and the sensor is electrically connected to a device for determining the level of electrical current "sensed" by the sensor (an electrical recorder, for example). The stimulatory electrode is thus used to "generate" electrical current and the sensor is thus used to "detect" electrical current. Note that the stimulatory electrode can be used to "generate" electrical current, which is itself a defined "gastrointestinal action", but the generation of electrical current can also produce other gastrointestinal actions (such as, for example, stomach contraction or esophageal pressure). The language "generating" GI action is thus intended to cover both concepts, i.e. the generation of the initial electrical current and the ultimate gastrointestinal action which is "generated" as a result of the current (i.e. the contraction or pressure).

"Operatively connected" is used herein to refer to the connection between the stimulatory electrode and the sensor, and indicates that the operation of one is connected to the operation of the other. In particular, the sensor connects to a device which determines the level of electrical current sensed by the sensor. A representation of that level is then fed to the source of electrical current that is electrically connected to the stimulatory electrode. The source of electrical current is provided with a programmable computer circuit that enables the level from the sensor to determine, or dictate, the operation of the source (i.e., electrical current is generated by the source and fed through the stimulatory electrode in response to and an in relation to the amount of the level of electrical activity sensed by the sensor). Thus, the "operatively connected" stimulatory electrode and sensor enable the retrograde feedback concept to occur.

Figure 9:
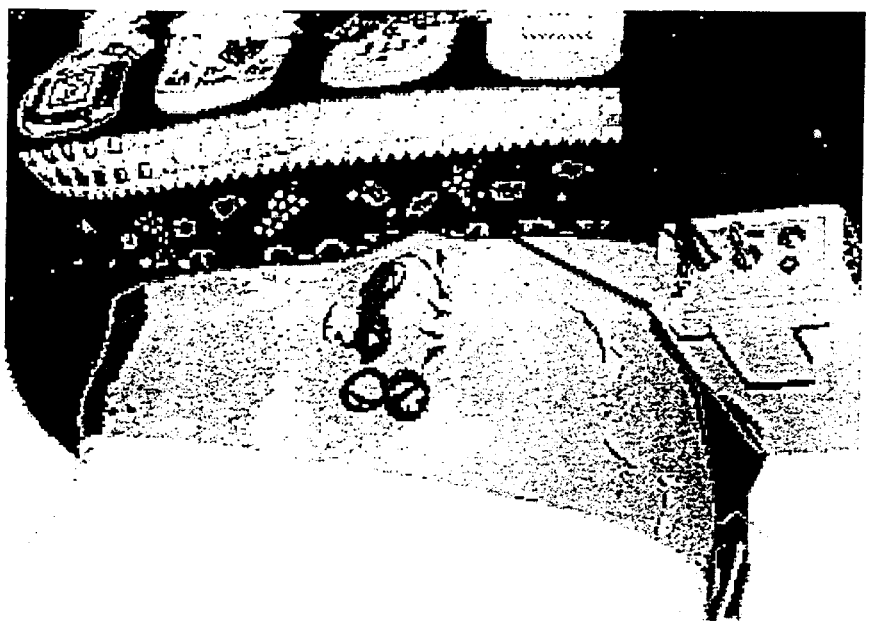
FIG. 9 illustrates a typical portable pacemaker in use.
Figure 10:
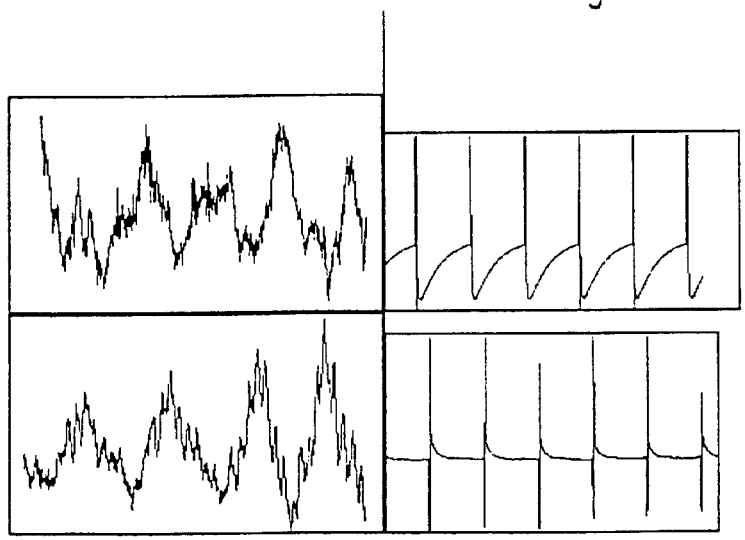
FIG. 10 illustrates gastric pacing in a rat.
Figure 16:
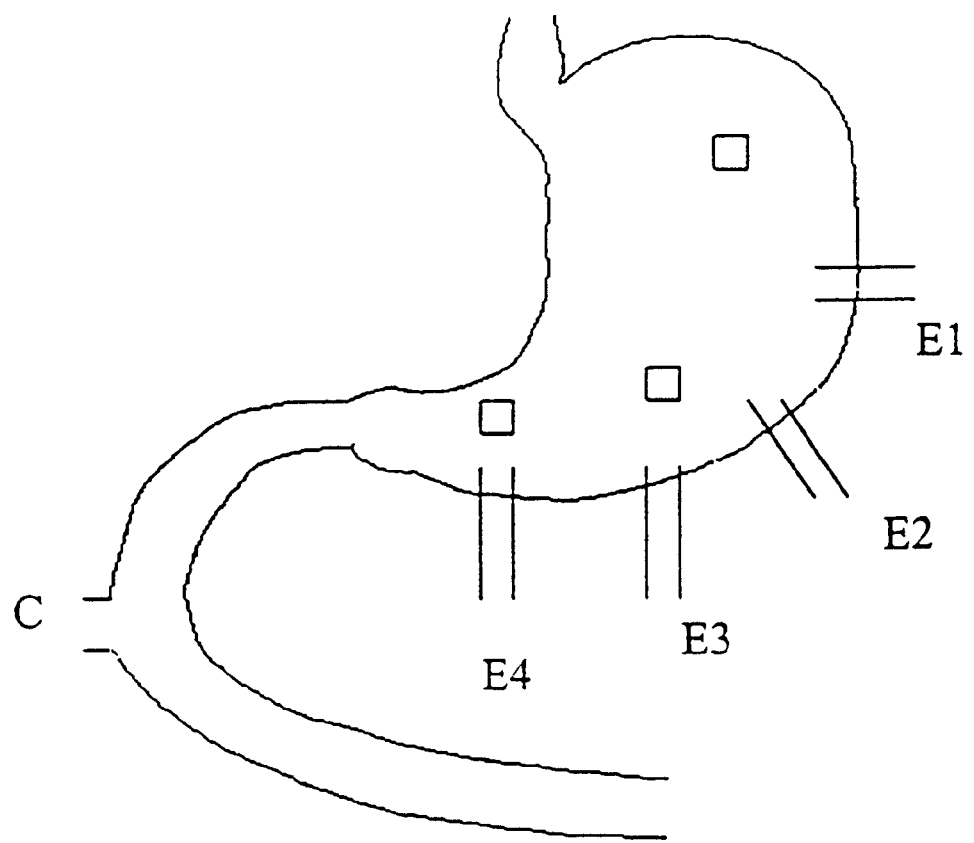
FIG. 16 illustrates the connection of electrodes to a dog stomach.

"Positioning" a stimulatory electrode or a sensor refers to placement of the stimulatory electrode or sensor on or in a subject. In the example of gastrointestinal pacing, the teflon-coated wires which are the stimulatory electrode and the sensor can be "positioned" as shown in FIGS. 9 and 16.

"Periodically" refers to evenly or unevenly spaced time intervals.

"Differs from" refers to a statistically significant variation between two compared values, and therefore does not always require a difference in orders of magnitude. It should be apparent that where small values are compared, statistically significant variations can likewise be very small, and where large values are compared, statistically significant variations can be large. Conversely, "substantially equals" refers to a statistically insignificant variation between two compared values.

"Reducing weight" refers to a reduction or decrease in weight of a subject.

"Electrical field stimulation" refers to the generation of an "electrical field", which indicates that the area of distribution of the electrical current from the stimulation encompasses the entire area between and/or surrounding two or more stimulatory electrodes, and "field" is used to imply that the two or more stimulatory electrodes are positioned at least about three centimeters apart (thus the term "field" to differ from prior stimulations where the two electrodes of a pair are positioned in close proximity to one another and do not generate a "field")

A "device" refers to any suitable item which can readily be and is desirable to be placed in the GI tract. Such devices can include, for example, stimulatory electrodes and sensors for use in the RGES method of the subject invention. Such devices could also include a small balloon to be used to provide pressure within the esophagus or small/large intestine. A small gauge for measurement of pressure could be a device in accordance with the subject invention.

With these definitions in mind, the subject invention provides a method of regulating gastrointestinal action in a subject. The method comprises determining an optimum level of total gastrointestinal action in a subject, the total gastrointestinal action including naturally occurring gastrointestinal action and non-naturally occurring gastrointestinal action; positioning a stimulatory electrode relative to the subject so that the stimulatory electrode can generate non-naturally occurring gastrointestinal action; positioning a sensor relative to the subject so that the sensor senses the level of total gastrointestinal action, the sensor being operatively connected to the stimulatory electrode; periodically detecting the level of total gastrointestinal action with the sensor; and periodically generating non-naturally occurring gastrointestinal action with the stimulatory electrode when the detected level of total gastrointestinal action differs from the optimum level until the detected level of total gastrointestinal action substantially equals the optimum level.

The invention further provides a method for reducing weight in a subject having a stomach. The method comprises determining an optimum level of total stomach electrical activity in a subject which reduces weight in the subject, the total stomach electrical activity including naturally occurring stomach electrical activity and non-naturally occurring stomach electrical activity; positioning a stimulatory electrode relative to the subject so that the stimulatory electrode can generate non-naturally occurring stomach electrical activity; positioning an electrical activity sensor relative to the subject so that the electrical activity sensor senses the level of total stomach electrical activity, the electrical activity sensor being operatively connected to the stimulatory electrode; periodically detecting the level of total stomach electrical activity with the electrical activity sensor; and periodically generating non-naturally occurring stomach electrical activity with the stimulatory electrode when the detected level of total stomach electrical activity differs from the optimum level until the detected level of total stomach electrical activity substantially equals the optimum level.

Also provided is a method of providing electrical field stimulation to a gastrointestinal organ. The method comprises positioning a first stimulatory electrode in a gastrointestinal organ; positioning a second stimulatory electrode in the gastrointestinal organ, the second stimulatory electrode being positioned at least about two centimeters from the first stimulatory electrode; and electrically stimulating the gastrointestinal organ simultaneously through the first and the second stimulatory electrodes, wherein one of the first and the second stimulatory electrodes has a positive polarity and wherein the other one of the first and the second stimulatory electrodes has a negative polarity, thereby providing electrical field stimulation to the gastrointestinal organ between the first and the second stimulatory electrodes. In further embodiments, the second stimulatory electrode is positioned at least about three centimeters, at least about five centimeters, or at least about ten centimeters from the first stimulatory electrode.

Additionally provided is a method of providing electrical potential gradient in a gastrointestinal organ. The method comprises positioning a first stimulatory electrode in a gastrointestinal organ; positioning a second stimulatory electrode in the gastrointestinal organ, the second stimulatory electrode being positioned at least about two centimeters from the first stimulatory electrode; and electrically stimulating the gastrointestinal organ simultaneously through the first and the second stimulatory electrodes, wherein voltage generated by the first stimulatory electrode differs from voltage generated by the second stimulatory electrode, thereby providing an electrical potential gradient in the gastrointestinal organ between the first and the second stimulatory electrodes. In further embodiments, the second stimulatory electrode is positioned at least about three centimeters, at least about five centimeters, or at least about ten centimeters from the first stimulatory electrode.

The invention further provides a method of stimulating the vagus nerve of a subject. The method comprises positioning a stimulatory electrode in a gastrointestinal organ of a subject; and generating electrical current in the gastrointestinal organ of the subject with the stimulating electrode, wherein the electrical current in the gastrointestinal organ of the subject stimulates the vagus nerve of the subject.

The invention also provides a method of placing a device in the gastrointestinal tract of a subject from the exterior of the subject. The method comprises inserting an end of a needle having an interior bore from the exterior of a subject into the gastrointestinal tract of the subject, the gastrointestinal tract of the subject having a center defined by a wall, the wall having a thickness defining an interior wall adjacent to the center and an exterior wall, and the end of the needle being inserted through the wall into the center of the gastrointestinal tract; inserting a device through the interior bore of the needle, wherein the device has an interior wall engaging means and wherein the device is inserted at least until the interior wall engaging means extends beyond the interior bore of the needle; removing the needle; and retracting the device until the interior wall engaging means engages the interior wall of the gastrointestinal tract of the subject, thereby placing the device in the gastrointestinal tract of the subject. Alternatively, the invention provides a method of placing a device in the gastrointestinal wall of a subject from the exterior of the subject. This method comprises inserting an end of a needle having an interior bore from the exterior of a subject into the gastrointestinal wall of the subject, the gastrointestinal wall defining a center of a gastrointestinal tract of the subject, the gastrointestinal wall having a thickness defining an interior wall adjacent to the center and an exterior wall, and the needle being inserted until the end of the needle is positioned in the thickness of the wall between the interior wall and the exterior wall; inserting a device through the interior bore of the needle, wherein the device has an engaging means and wherein the device is inserted until the engaging means extends beyond the interior bore of the needle into the thickness of the wall; removing the needle; and retracting the device until the engaging means engages the thickness of the wall, thereby placing the device in the gastrointestinal wall of the subject.

In one embodiment, the electrical stimulator so placed extends throughout the thickness of the wall of the gastrointestinal tract. For example, the electrical stimulator can be placed in the stomach of the gastrointestinal tract and can therefore be so placed as to extend throughout the thickness of the wall of the stomach.

In one embodiment, the interior wall engaging means comprises a plurality of radially extendable arms positioned at an axis perpendicular to the insertion axis of the electrical stimulator. The electrical stimulator is inserted until the axis of the plurality of radially extendable arms extends beyond the interior bore of the needle, at which point the arms radially extend. The electrical stimulator is retracted until the radially extended arms engage the interior wall of the gastrointestinal tract.

MATERIALS AND METHODS

Preparation of Dogs.

Healthy female (males are excluded since they would wet the jacket during urination) hound-dogs are used in this study. The dog is chosen to be the model for this study because: 1) the patterns of gastric myoelectrical activity and motility in dogs are the same as those in humans; and 2) the canine model has been used for the investigation of gastrointestinal motility for many years, and experimental results indicated that this animal model is ideal for motility studies.

After an overnight fast, the dog is operated upon under anesthesia. Approximately thirty minutes prior to induction of anesthesia, the dog is pre-medicated with acepromazine maleate (2 ml subcutaneously) and atropine (1 mg subcutaneously). Anesthesia is induced with thiamylal sodium (30 ml/kg, intravenously). Following induction of anesthesia and endotracheal incubation, anesthesia is maintained for surgery using 1.5 to 2.0% isoflurane in oxygen-nitrous oxide (1:1) carrier gases delivered from a ventilator (15 breaths/min with a titred volume of about 15 ml/kg). The animal is monitored with the assessment of tissue color and pulse rate. Four pairs of bipolar recording electrodes (cardiac pacing wires) are implanted on the serosal surface of the stomach along the greater curvature at an interval of 4 cm (see FIG. 16). The most distal pair is 2 cm above the pylorus. The distance between the two electrodes in a pair is 0.5 cm. Teflon-insulated wires are brought out through the abdominal wall subcutaneously and placed under a sterilized dressing until needed for recording and stimulation studies. Three strain gauges are placed, one in the fundus, one in the proximal antrum, and the other in the distal antrum, for the measurement of fundic tone and antral contractions. The wires of these strain gauges are brought out the same way as the electrodes. An intestinal fistula is made in the duodenal (20 cm beyond the pylorus). The fistula is used for the assessment of gastric emptying of liquids.

Following completion of surgery, the anesthetic gases are discontinued, and ventilation is continued with oxygen until the dog regains airway reflexes and is extubated. After extubation, the dog receives medications for post operative pain control and is transferred to a recovery cage. All studies are initiated about ten days after surgery when the dogs have completely recovered. A dog jacket and protective plastic collar are worn all the time to protect the wires and cannula from being chewed out by the dog.

Measurement and analysis of gastric slow waves.

The gastric slow wave are measured from the implanted serosal electrodes using a multi-channel recorder (Acknowledge, Biopac Systems, Inc., Santa Barbara, Calif.). All signals are displayed on a computer monitor and saved on the hard disk by an IBM- compatible 486 PC. The low and high cutoff frequencies of the amplifier are set at 0.05 Hz and 10 Hz respectively. The data is sampled at 20 Hz. For the spectral analysis of the slow waves, all data is further lowpass filtered with a cutoff frequency of 1 Hz (Qian et al. 1999; Abo et al. 2000).

Percentage of normal slow waves: The percentage of normal slow waves is defined as the percent of time during which regular slow waves (3.5–7.0 cpm) are detected from the time-frequency analysis of the slow wave measurement. This parameter reflects the regularity of gastric slow waves and is computed using the time-frequency analysis method discussed below (see also Chen et al. 1993). In the outcome-based feedback-controlled RGES system, this parameter is on-line computed and used to control the strength of stimulation.

Percentage of slow wave coupling: This parameter represents the coordination or coupling of gastric slow waves measured from different regions of the stomach. It is defined as the percentage of time during which the recorded slow waves in different regions are coupled. A cross-spectral analysis method is used to calculate the percentage of slow wave coupling among the different channels. First time-frequency analysis is performed on each channel minute by minute and the frequency of each minute of the slow wave in each channel is determined. Secondly, the frequencies of the slow waves between any two channels are compared. The minute of the slow waves recorded on the two channels is defined as coupled if their dominant frequencies are both within the normal frequency range and their difference is <0.2 cpm.

Measurement and analysis of gastric contractions.

Gastric contractions in the fundus, proximal antrum and distal antrum are measured using the surgically implanted strain gauges as shown in FIG. 16. The recordings are made using the same multi-channel recorder used for the electrical recordings. Computerized software computes the frequency of contractions and the strength of contractions (area under the curve of each identified contraction).

Measurement and analysis of vagal activity.

Regular electrocardiogram (ECG) is recorded using abdominal surface electrodes. R-R intervals are derived from the ECG using a method of fuzzy neural network. A signal, called heart rate variability (HRV), is derived after interpolation and sampling. Smoothed power spectral analysis is then performed on the HRV signal. Two parameters are computed from the power spectrum: LF (area under the curve in the low frequency band (0.04–0.15 Hz)) and HF (area under the curve in the high frequency band (0.15–0.50 Hz)). It is well established that the LF reflects mainly sympathetic activity and partial vagal activity, where the HF represents purely vagal activity (Lu et al. 1999). In addition, the ratio, LF/HF, represents sympatho-vagal balance.

Measurement of "symptoms" in dogs.

The symptoms of the dog during the experiment to be evaluated include salivation, licking tongue, murmuring (whine, growl, bark, yelp), and moving due to discomfort, and are scored by their severity and/or frequency. The severity is classified into 4 degrees, none (0), mild (1), moderate (2), and severe (3). For salivation, none is 0, seen around mouth is 1, sometimes drop is 2, and continuously drop is 3. For licking tongue and murmuring, none is 0, seldom/seen for <25% time of study is 1, often/seen for <50% time of study is 2, and severe/seen for >50% time of study is 4. For movement due to discomfort, none/same as baseline is 0, mild/seen but no need to soothe is 1, moderate/seen and need to soothe is 2, and severe/dog jumps, or moves constantly to interrupt study is 3. Vomiting is noted separately and scored as 4. A total symptom score is calculated.

EXAMPLE I

Antegrade Electrical Stimulation

Extensive experiments on antegrade gastric and intestinal electrical stimulation have been performed in both animals and humans. Unlike the retrograde stimulation proposed in this application, these studies were designed to normalize impaired gastrointestinal motility. The most important points learned from these experiments are: 1) electrical stimulation is able to entrain slow waves; 2) antegrade stimulation accelerates gastric emptying; and 3) no adverse effects have been noted in these previous studies, demonstrating safety of electrical stimulation.

Antegrade electrical stimulation entrains slow waves.

A number of recent systematic studies have been performed and indicated that a complete entrainment of gastric slow waves is feasible in both humans and dogs (Lin et al. 1998; Lin et al. 2000a; McCallum et al. 1998; Qian et al. 1999; Abo et al. 2000; Lin et al. 2000b). The pulse width used for the entrainment of gastric slow waves in patients with gastroparesis was about 300 ms. However complete entrainment is limited to a pacing frequency of slightly higher than the intrinsic frequency of the gastric slow wave. The entrainment was 100% when the pacing frequency was 10% higher than the intrinsic frequency and dropped to about 70% when the pacing frequency was 30% higher. In addition, the maximal driven frequency was about 4.3 cpm in patients with gastroparesis (Lin et al. 1998).

Antegrade electrical stimulation normalizes dysrhythmia.

Figure 4:
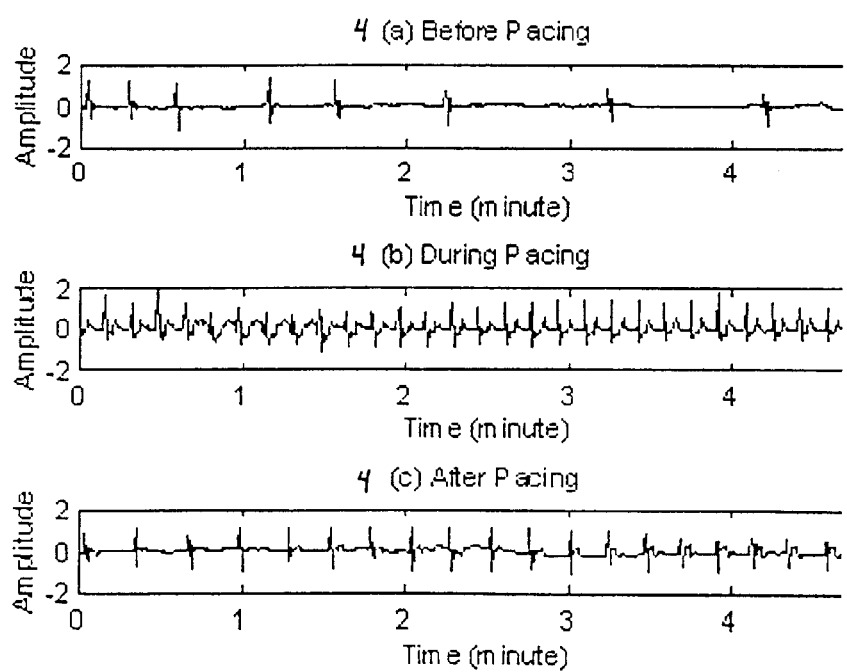
FIGS. 4A–4C illustrate normalization of bradygastria using gastric electrical stimulation.

Entrainment of gastric slow waves using electrical stimulation with long pulses (in the order of milliseconds) makes it possible for the normalization of gastric dysrhythmia. Recent canine studies have also shown that gastric electrical stimulation was able to normalize gastric dysrhythmia induced by various pharmacological agents, such as vasopressin, glucagon and atropine (Qian et al. 1999). FIGS. 4A–4C show a typical example of impaired gastric slow waves (bradygastria, FIG. 4A) induced by atropine and normalized slow waves after gastric pacing (FIG. 4C).

In addition to gastric entrainment, it has also been shown that intestinal slow waves can be entrained using intestinal pacing with long pulses (Lin et al. 2000a; Lin et al. 2000b).

Antegrade electrical stimulation accelerates gastric emptying in patients with gastroparesis.

Figure 5:
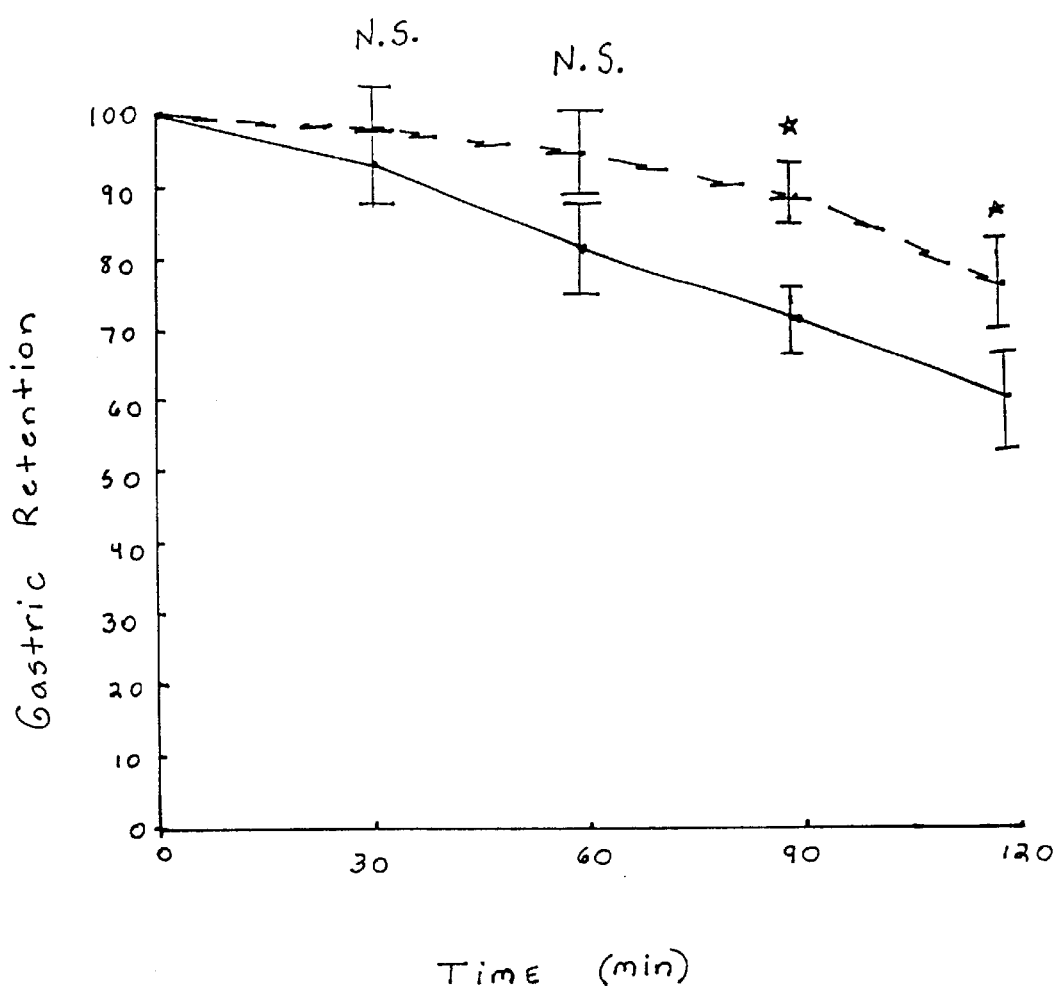
FIG. 5 illustrates the effect of gastric pacing on retention of a radionuclide solid meal.

The effect of electrical stimulation on gastric emptying and symptoms in patients with severe gastroparesis has been investigated (McCallum et al. 1998). Electrical stimulation was performed via serosal electrodes implanted on the proximal stomach. A portable external pacemaker was built and used for stimulation for one month or more in each patient. A significant improvement was observed in both gastric emptying (FIG. 5) and symptoms of nausea, vomiting, bloating and etc.

Gastrointestinal electrical stimulation does not induce any adverse events.

The above study not only suggested the therapeutic potential of antegrade gastric electrical stimulation for gastroparesis but also demonstrated the safety of gastric electrical stimulation in humans. No side effects or adverse events were noted in this clinical study. Chen and his colleagues have performed gastrointestinal electrical stimulation in more than 15 patients with gastroparesis and more than 30 dogs over the course of 7 years (Lin et al. 1998; Lin et al. 2000a; McCallum et al. 1998; Qian et al. 1999; Abo et al. 2000; Lin et al. 2000b). No adverse events have been observed in the patients. Some of the patients were studied for more than 4 months. Similarly, no gastrointestinal symptoms, such as vomiting or diarrhea, or other symptoms have been observed in dogs. Autopsy was performed in every dog that was sacrificed at the end of the study. No scars or muscle damage were noted in the gastric or intestinal area where stimulation electrodes were sutured. Some of the dogs have been studied for a period of 6 months or more.

EXAMPLE II

Retrograde Electrical Stimulation (RGES) for Treatment of Obesity and Other Gastrointestinal Tract Disorders This example places an artificial ectopic pacemaker in the distal antrum to partially or completely override regular gastric slow waves with a feedback control mechanism. Two pairs of bipolar electrodes are placed on the serosa along the greater curvature laparoscopically. The distal pair is about 2 cm above the pylorus and is used for electrical stimulation (serving as an artificial pacemaker), whereas the proximal pair is about 10 cm above the pylorus and is used for the measurement of gastric slow waves. The regularity of gastric slow waves is calculated from the proximal pair and the strength of electrical stimulation applied on the distal pair is determined based on the regularity of gastric slow waves measured from the proximal pair. The targeting regularity is set up in the initial trial period such that the intake of food is reduced but the subject is free of any symptoms other than early satiety. Once this value is determined, the value is used to automatically control the strength of electrical stimulation.

Figure 2:
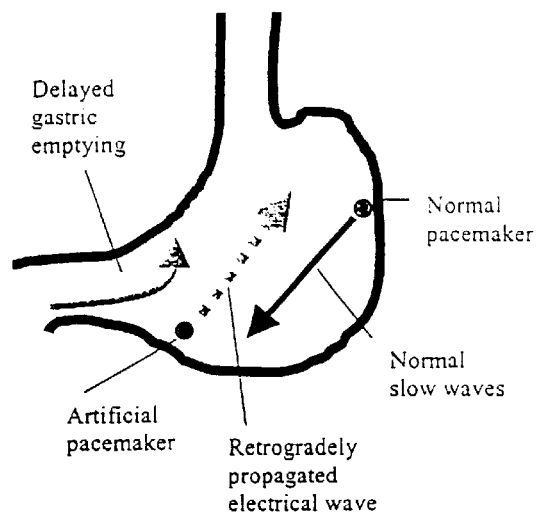
FIG. 2 illustrates the retrograde electrical stimulation (RGES) of the stomach to retard the propulsive activity of the stomach and slow down gastric emptying.

The principle of RGES is the opposite of what has been described for patients with impaired gastric emptying. RGES employs retrograde pacing with the aim of retarding the propulsive activity of the stomach and slowing down gastric emptying (FIG. 2). By slowing down gastric emptying of ingested food from the stomach, a sense of feeling full (satiety) results, leading to a reduction in food intake and subsequent weight loss.

Figure 3:
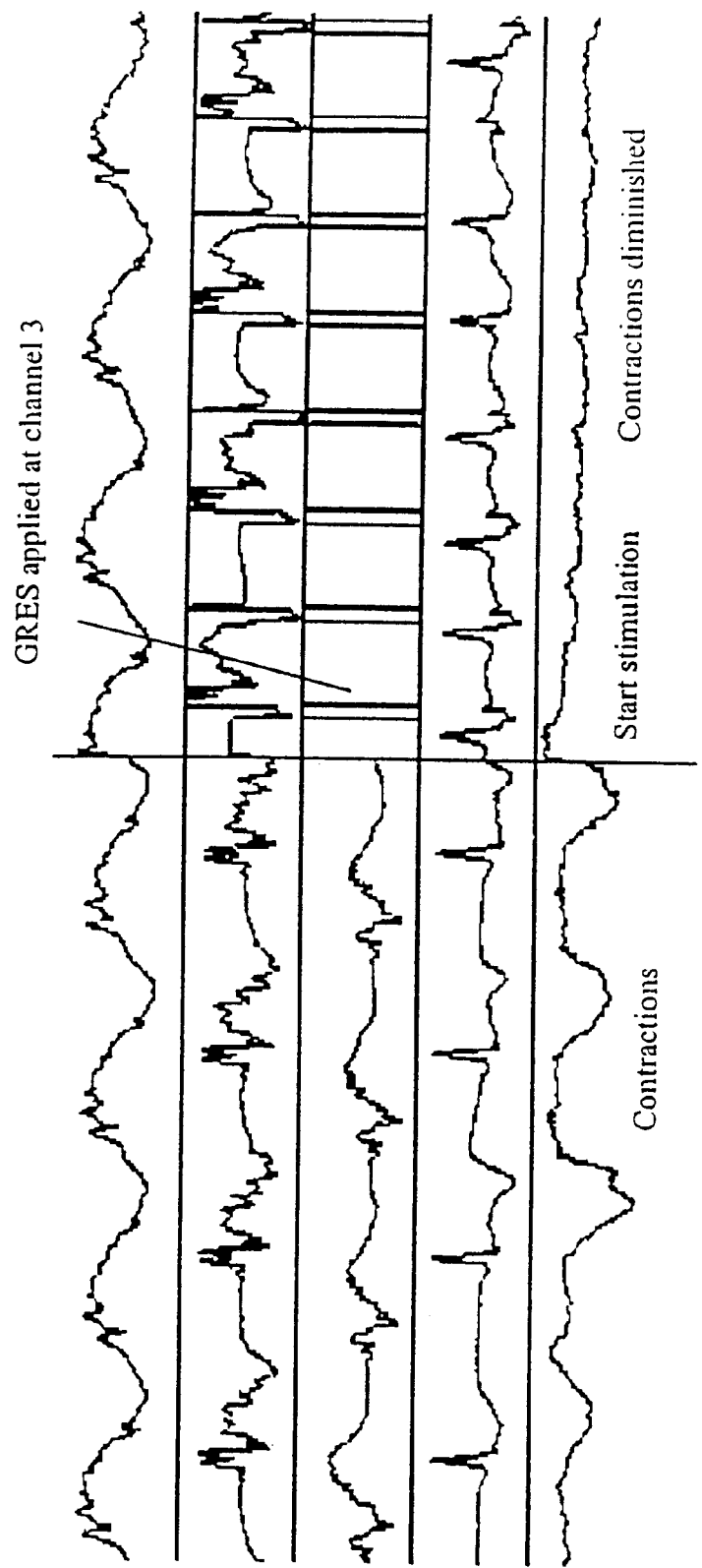
FIG. 3 illustrates the effects of RGES at a tacygastrial frequency on gastric slow waves and contractions in a healthy dog.

The rationale behind RGES at a tachygastrial frequency is to electrically induce tachygastria in the distal stomach, in effect producing an artificial ectopic pacemaker. This artificial pacemaker has two functions: 1) it interrupts the normal distal propagation of regular slow waves; and 2) it paces the gastric slow waves in the distal stomach at a tachygastrial rhythm. Both of these effects result in an absence of contractions in the distal stomach (see FIG. 3) and cause delayed gastric emptying. This results in increased satiety and decreased food intake. This method allows adjustment of the strength of electrical stimulus, and hence the degree of impairment in the gastric slow wave and its propagation. Thus, with proper settings, the amount of food intake can be finely tuned.

RGES at a "physiological" frequency reduces food intake.

A study was performed to investigate the effects of RGES on gastric emptying and food intake. The study was performed in 10 healthy dogs with chronically implanted 4 pairs of serosal electrodes along the greater curvature: the 3 proximal pairs recorded gastric slow waves and the most distal pair (2 cm above the pylorus) provided retrograde stimulation. Each dog was studied in 3 sessions, without electrical stimulation (session 1), with strong retrograde stimulation to induce vomiting or noticeable symptoms (session 2) and with mild retrograde stimulation that does not induce vomiting or clearly noticeable discomfort (session 3). Electrical stimulation was performed at a frequency 10% higher than the intrinsic frequency of gastric slow waves measured at baseline. The dogs were given unlimited access of food during the study. All observable symptoms were noted and graded.

Figure 6:
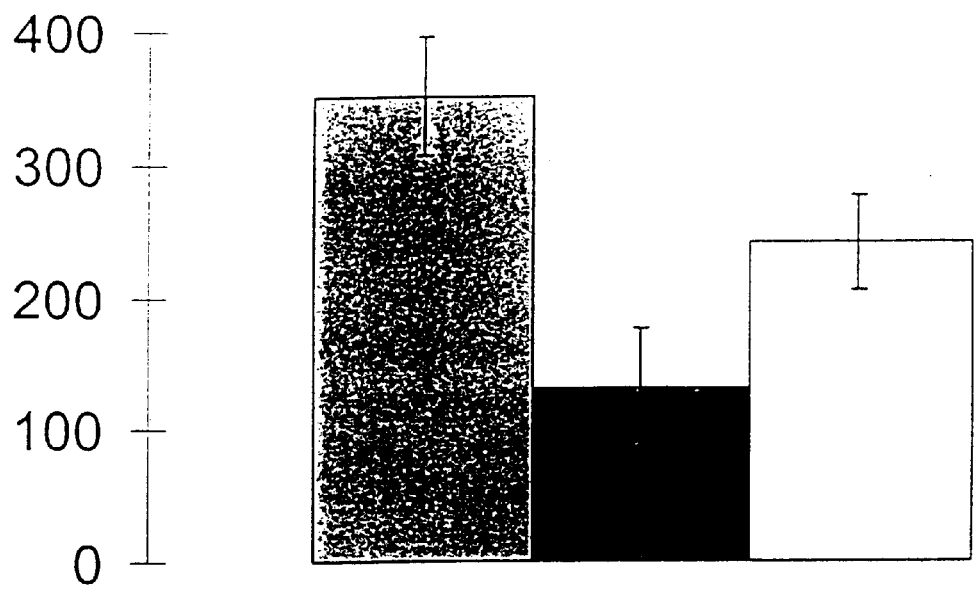
FIG. 6 illustrates food intake in separate sessions with varying amounts of electrical stimulation.
Figure 7:
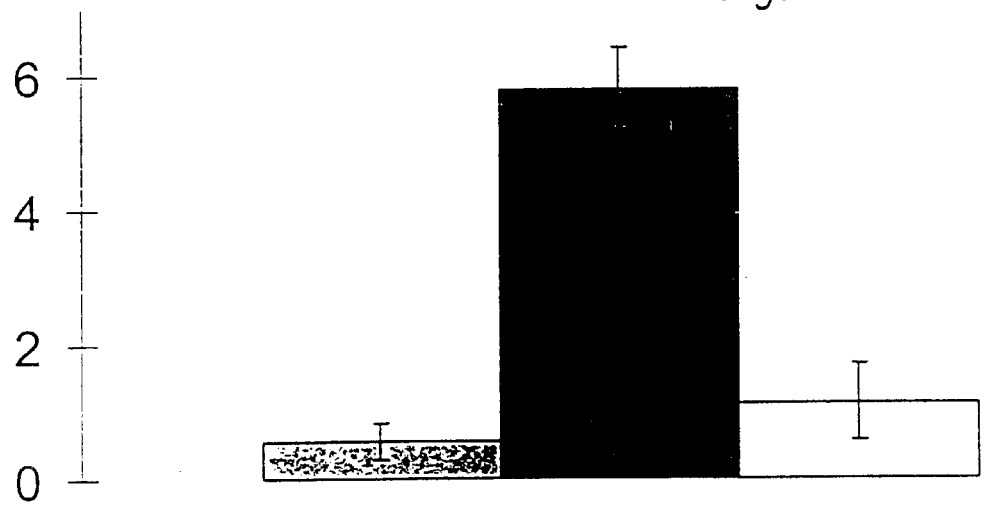
FIG. 7 illustrates symptoms seen in the separate sessions of FIG. 6.

RGES resulted in a significant reduction in food intake (FIG. 6). With strong retrograde stimulation (session 2), eight dogs vomited and all dogs showed various symptoms (see Materials and Methods). On the other hand, with mild stimulation (session 3), while inducing no vomiting and no significant increase in the score of other observable symptoms, food intake was significantly reduced (FIG. 7).

This study demonstrates that RGES with appropriate stimulus is able to reduce food intake without inducing discomfort or vomiting.

RGES at a "physiological" frequency also impairs slow wave propagation and delays gastric emptying.

Figure 8A:
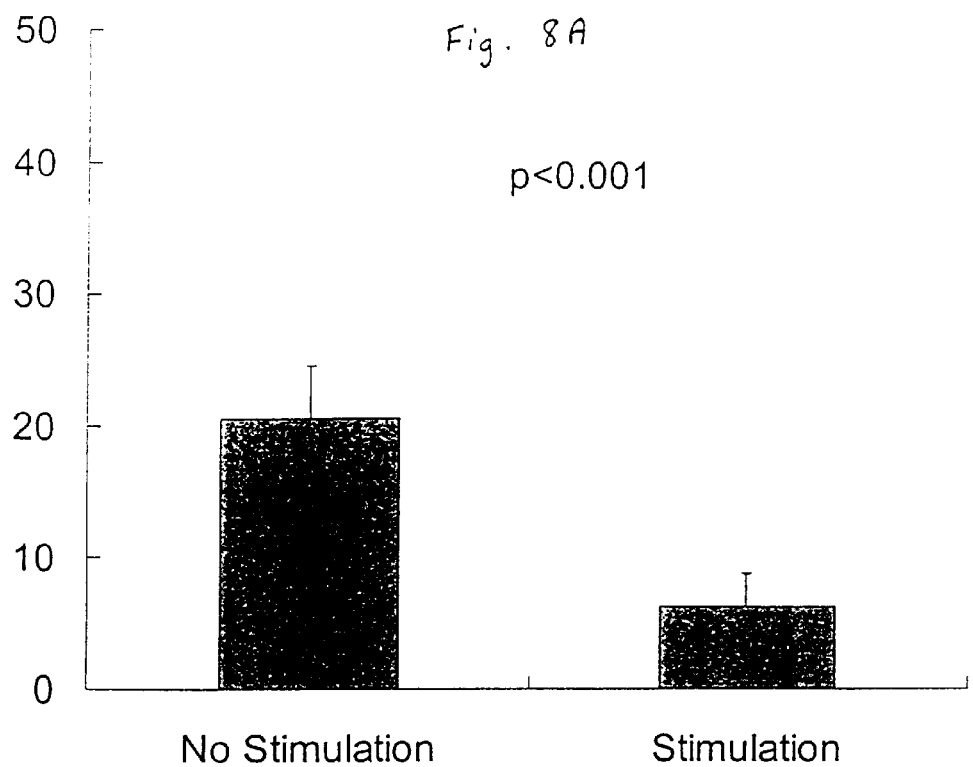
FIGS. 8A and 8B illustrate the effect of RGES at the normal frequency on gastric emptying and slow wave coupling.
Figure 8B:
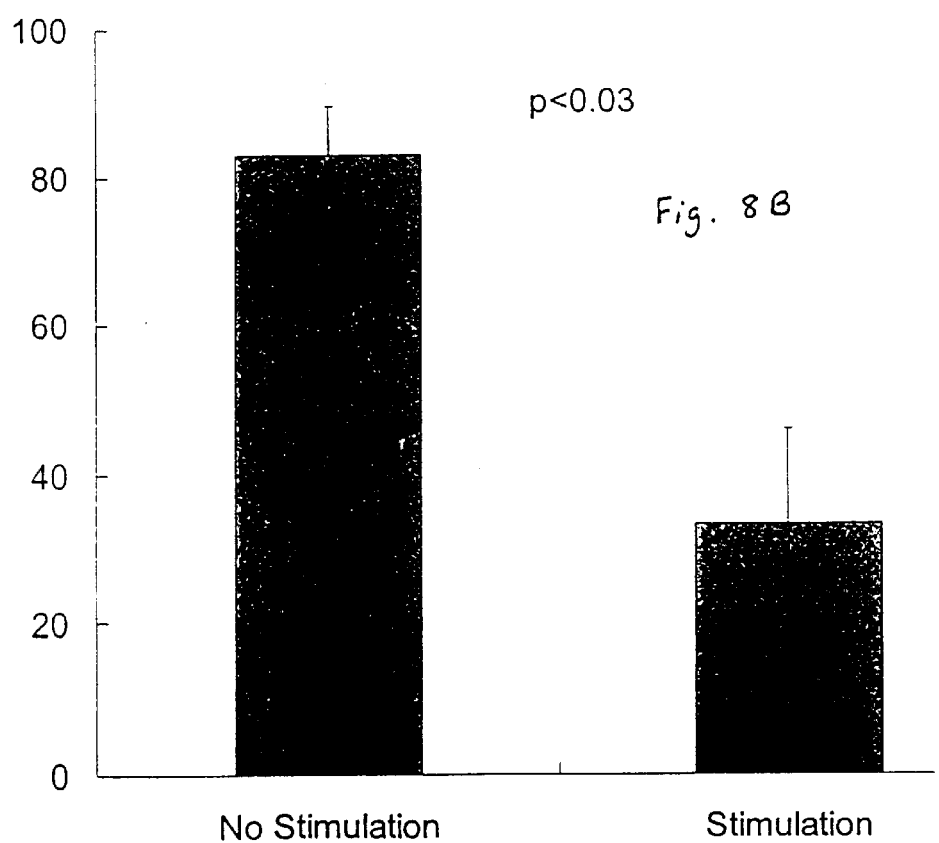

In addition to the above study, the effect of RGES at a normal frequency on gastric slow waves and gastric emptying was investigated in a separate study (Lin et al. 1999). The experiment was performed in 6 dogs implanted with gastric serosal electrodes as before and equipped with a duodenal cannula for the assessment of gastric emptying (see Materials and Methods). After the ingestion of a liquid meal, electrical stimulation was performed via the distal electrodes with a frequency of 10% higher than the intrinsic frequency of the gastric slow wave. It was found that gastric emptying (30 minutes after eating) was significantly delayed with RGES in comparison with the control session (FIG. 8A). This was accompanied by a significant impairment in gastric slow wave coupling (see Materials and Methods) (FIG. 8B).

This study suggests that the reduction in food intake observed in the feasibility study presented above is attributed to the impairment in gastric emptying and gastric slow wave propagation.

RGES at a tachygastrial frequency inhibits gastric contractions.

While RGES at a physiological frequency is effective in delaying gastric emptying and reducing food intake, it is limited in its practical utility because of the high level of energy required. The stimulation pulse width used is about 300–500 ms which is about one thousand times higher than that in cardiac pacing, implying a substantial amount of energy consumption. To overcome this energy consumption issue, RGES at a tachygastrial frequency can be used to achieve the same effects as above. A lower, and possibly much lower, energy is required for RGES at a tachygastrial frequency than for RGES at a normal frequency. RGES at tachygastrial frequency is even more efficient because it not only impairs distal propagation of gastric slow waves but also induces tachygastria in the stomach and further reduces gastric contractions.

In a further experiment, a dog was implanted with 4 pairs of gastric serosal electrodes along the greater curvature and a strain gauge close to the most distal pair of electrodes (2 cm above the pylorus). RGES was performed using the third pair of electrodes (6 cm above the pylorus) at a frequency of 11 cpm (the intrinsic frequency in the dog was about 6 cpm) and a pulse width of 50 ms. As shown in the left half of FIG.

3, normal distally propagated slow waves (top 4 tracings) and regular gastric contractions (bottom tracing) were observed at baseline. After stimulation (right half of FIG. 3), however, the frequency of gastric slow wave in channel 4 was increased and gastric contractions were diminished. This experiment was repeated several times in the same dog with the same results.

In the RGES procedure, each dog undergoes gastrointestinal pacing during at least 3 separate sessions. These include a "control" session (no stimulation), a "pacing" session (electrical stimulation resulting in a complete entrainment of gastric slow waves in at least one channel adjacent to the stimulation electrodes is called "pacing"), and one or more "optimization" sessions with stimulation energy reduced from the pacing session. Two consecutive sessions are at least 3 days apart.

The protocol for the control session (no electrical stimulation) is as follows (sequentially): a 30-min baseline recording, 30-min with access to unlimited regular solid food (the same food used in daily care of the animal) and water, 60-min postprandial recording after the removal of the food and water.

The protocol for the pacing session is composed of 30-min baseline recording, 15-min RGES, 30-min with access to unlimited food and water with RGES, 60-min postprandial recording with RGES after the removal of food and water. Electrical stimulation parameters are chosen to completely entrain gastric slow waves in the channel adjacent to the stimulation electrodes. Based on the experiments, the following parameters are able to entrain gastric slow waves: stimulation frequency—13 cpm (the normal frequency in the dog is about 5–6 cpm); pulse (square wave) width—500 ms; and pulse amplitude—4 mA (constant current is used in all experiments). A small adjustment is necessary for each particular dog and this is done at the beginning of stimulation by visually inspecting whether the paced slow waves are phase-locked with the stimulus.

The protocol for the optimization sessions is the same as the "pacing" session. However, electrical stimulation is performed with a reduced energy. More than one session is required to optimize the performance of GRES by changing stimulation parameters. The definition of optimization is based on an optimal combination of efficacy, safety and feasibility. That is, the optimal RGES settings are those that result in a significant reduction in food intake (efficacy) but do not induce undesired symptoms, such as nausea or vomiting (safety) with minimal energy (maximally feasible for an implantable device). Iterative adjustments of stimulation parameters are made to achieve this result.

Measurements made during the entire experiment include: food intake, all observable "symptoms", gastric myoelectrical activity, gastric contractions (including fundic tone), gastric compliance, and electrocardiogram. A detailed description of the measurements and analyses of these parameters is provided under the Materials and Methods section.

Analysis of variance (ANOVA) is performed to study the difference in food intake and symptom score (quantitative analysis is described under Materials and Methods) among the control, pacing and stimulation sessions. Effects of RGES on gastric slow waves and gastric contractions is also assessed.

The "pacing" session results in a substantial reduction of food intake but moderate to severe symptoms, such as vomiting. The optimal stimulation session results in a similar reduction of food intake with absolutely no vomiting, and no significant increase in other symptoms in comparison with the control session. The ideal result is a significant and substantial reduction in food intake with absolutely no uncomfortable symptoms and minimal consumption of energy (comparable with that in cardiac pacing).

By contrast with conventional methods of electrical stimulation, this RGES system contains two important additional elements: detection of the outcome of stimulation; and automated control of stimulation based on a pre-determined target (or "prescription"). The pre-determined target is the percentage of impairment of slow waves (=100%−% normal 3.5–7.0 cpm slow waves) measured by the sensing electrodes.

Figure 12:
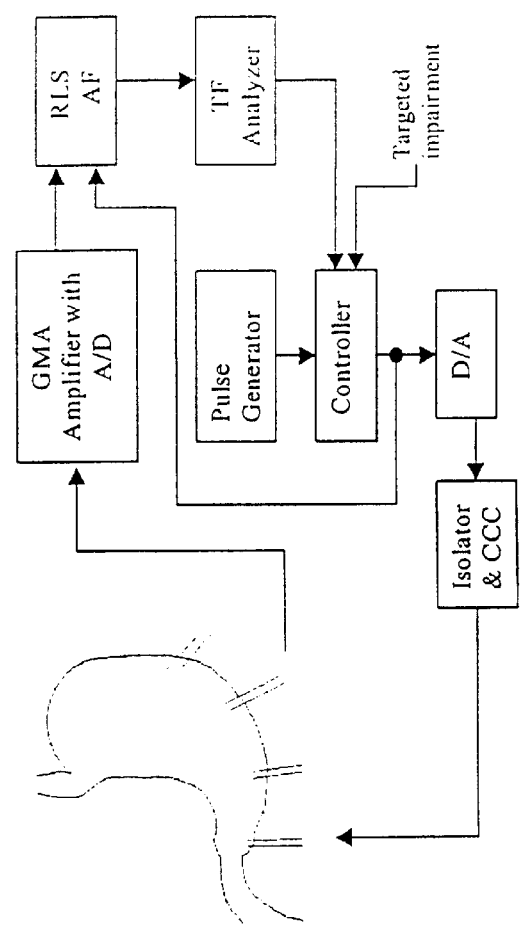
FIG. 12 is a block diagram of a typical RGES system.

FIG. 12 presents the block diagram of the system. The gastric slow wave is recorded with cutoff frequencies of 0.5 to 12 cpm by the sensing electrodes placed in the middle stomach and digitized at a frequency of 1 Hz (60 cpm). The digitized signal is subjected to digital signal processing. Since the recording of gastric slow waves may contain stimulation artifacts, the recording is first processed for the cancellation of stimulation artifacts with an adaptive filter using the recursive least squares (RLS) algorithm. Time-frequency analysis is performed on the artifacts-free gastric recording by the time-frequency analyzer and the percentage of normal gastric slow waves (or the percentage of impairment) is computed from the time-frequency representation. This percentage of impairment is then compared with the targeted impairment by a digital controller. If the computed percentage is within the range of ±5% of the target, the stimulation is maintained without any modification. If the computed percentage of impairment is lower than the target minus 5%, the stimulation energy or pulse width is increased by 10% or a smaller or larger step to be determined by experiments. If the computed percentage of impairment is higher than the target plus 5%, the pulse width is reduced by 10% or a smaller or larger step to be determined by experiments. The digital stimulus is converted into an analog signal by a D/A converter. A constant current control circuit is used to guarantee that constant current is delivered to the stimulation electrodes placed 2 cm above the pylorus.

Maximal and minimal thresholds for pulse width are determined by experiments and pre-set. An alarm is set off if one of the thresholds is reached and the stimulation is switched to a fixed parameter mode (using optimized parameters derived as discussed above). The maximal threshold is used to protect the subject from being hurt with excessive stimulation. The minimal threshold is introduced to protect the system from being ineffective and would be reached in two instances: 1) if the system malfunctions; and 2) if the percentage of normal gastric slow waves before stimulation in the subject is below the targeted impairment. Five minutes after stimulation with the fixed mode, the automatic system is turned on again.

The RGES system has the following advantages: 1) the stimulation is not fixed but dynamically modulated by the outcome of stimulation. It is much easier to optimize the performance in individual subjects than by the somewhat random process of using fixed parameters; 2) the physician can actually "prescribe" the "dosage" of treatment. For example, a higher "dosage" (higher percentage of impairment) may be "prescribed" at the beginning of treatment to loose sufficient weight, followed with a lower "dosage" to maintain weight loss.

Cancellation of stimulation artifacts.

Electrical stimulation artifacts are often superimposed on the gastric slow wave recording. These artifacts must be cancelled before the time-frequency analysis of the gastric slow wave. Otherwise, the computed percentage of impairment or normal 3.5–7.0 cpm slow waves would be inaccurate. Similar problems have been encountered and adaptive filtering has been applied for the cancellation of respiratory artifacts superimposed on the abdominal surface recording of gastric slow waves (Chen et al. 1989) or intestinal slow waves (Chen and Lin 1993).

Figure 13:
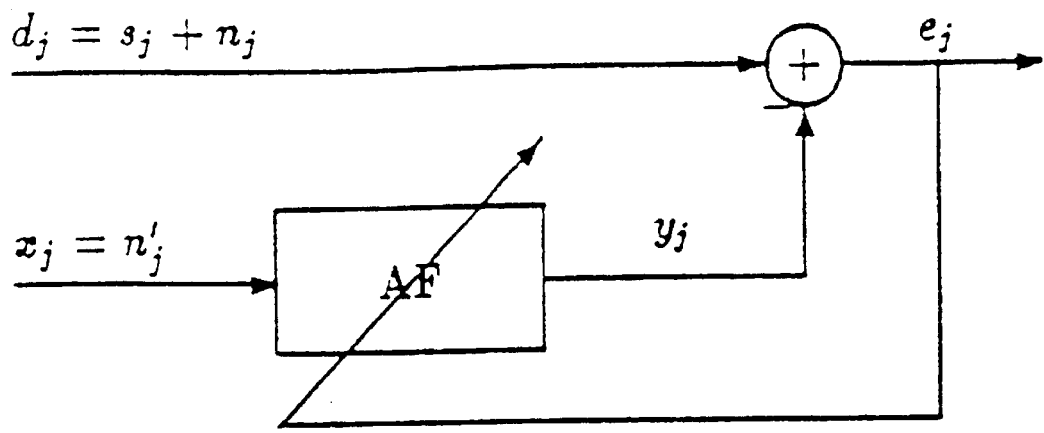
FIG. 13 is a block diagram of an adaptive filter.

The similar technique of adaptive filtering is used with RGES to cancel the stimulation artifacts. As shown in FIG. 13, $d_j$ represents the measurement of gastric slow waves by the sensing electrodes. It contains gastric slow waves ($s_j$) and stimulation artifacts ($n_j$). A reference signal $x_j$ is obtained directly from the stimulator. It is clear that this reference signal is closely correlated with the stimulation artifact, $n_j$, but may have a different phase and amplitude. An adaptive filter (AF) is used to adjust the amplitude and phase of the reference signal such that its output $y_j$ is identical to stimulation artifacts, $n_j$. Consequently, the subtracted output $e_j$ would be artifacts-free.

Various algorithms available for the adaptive filter can be used in this method, including least mean squares algorithm and recursive least squares (RLS) algorithm. The selection of the algorithm is based on the performance and the computational feasibility for an implantable device. An RLS algorithm is a good choice.

Time-frequency analysis of gastric slow waves.

Numerous methods are available in the literature for time-frequency analysis (Akay 1995). Short-time Fourier transform (STFT) is among the early works in this area. A sliding window with a short length is used in the STFT and the signal inside the window is assumed to be stationary. Wigner developed another approach (Wigner 1932) which was later adapted to signal processing by Ville (1948). In this case, a quadratic distribution of the time and frequency characteristics of the signal is derived. The major drawback of this representation is in its interpretation. That is, the representation not only contains the signal components but also interference terms, called cross-terms, generated by the interaction of these signal components with each other. Many suggestions have been made to improve the Wigner-Ville distribution, all using some kind of filtering process to enhance the signal components and to attenuate the interference terms. The exponential distribution proposed by Choi-Williams was one of them (Choi and Williams 1989). Cohen (1992) unified the quadratic time-frequency representations. He showed that most of them belonged to a general class, in which each member was generated by the choice of an appropriate kernel function. In the early 1980s, a theory that unified a set of ideas about analyzing a signal at different resolutions was proposed and was called wavelet representation (Rodet 1985; Grossman and Morlet 1984). An interesting characteristic of this method relies on its ability to behave like a mathematical microscope, that is, it can zoom in on short-lived signal components. The wavelet transform (WT) is a signal decomposition on a set of basis function, obtained by dilations, contractions, and shifts of a unique function, the wavelet prototype. A basic distinction between WT and STFT is that while the basic functions of the latter consist of a function of constant width translated in time and filled in with high-frequency oscillations, the former has a frequency-dependent width. In other words, it is narrow at high frequencies and broad at low frequencies. This gives the WT the ability to zoom-in on transitory phenomena, which are usually short-lived components of a signal.

Each of the above mentioned methods has been applied to the time-frequency representation of the gastric slow wave measured from electrogastrography. The STFT method was first introduced and is still being used by various investigators (Chen and McCallum 1995). With the EGG (electrogastrogram, abdominal surface measurement of gastric slow waves) signal sampled at 1 Hz, the STFT is typically performed with a window length of about 4 minutes and a shift of 1 minute between two consecutive Fourier transforms. The disadvantage of this method is its low temporal resolution. Abnormal slow waves with a brief duration can not be reliably detected.

The Wigner distribution and the exponential distribution were investigated (Lin and Chen 1994). The unmodified Wigner distribution was found inappropriate for the time-frequency analysis of the EGG due to inherent interference terms resulting from noises and interference present in the EGG. The exponential distribution provided much better performance than the Wigner distribution but was not satisfactory, especially when the EGG signal was noisy (Lin and Chen 1994). Its performance in the analysis of the gastric slow wave measured from the implanted serosal electrodes is expected to be better since the serosal recording does not contains much noise or artifacts. The WT method was recently applied in an attempt to identify contraction-related spike potentials in the EGG. However, no convincing data have been provided, suggesting that spike potentials are present in the EGG and that they can be detected using the WT method. In addition to these methods, a so-called adaptive spectral analysis method was developed which is based on the autoregressive moving average (ARMA) model and was implemented using an adaptive ARMA filter (Chen et al. 1990).

The various methods for the time-frequency analysis (or running spectral analysis) of the cutaneously recorded gastric slow waves (Chen et al. 1990; Chen et al. 1993; Lin and Chen 1994; Lin and Chen 1995; Wang et al. 1998; Lin and Chen 1996), or electrogastrography (EGG), are summarized as follows:

Autoregressive moving average (ARMA) modeling with adaptive filtering.

Gastric slow waves can be detected noninvasively using abdominal surface electrodes, a method called electrogastrography. The cutaneous measurement and display of gastric slow waves is called an electrogastrogram (EGG). The EGG contains elements of both gastric signal and noise (or interference) such as respiratory and motion artifact. Spectral analysis methods are used to derive clinically useful parameters from the EGG. Time-frequency analysis methods have been developed or applied for the quantitative assessment of the regularity of gastric slow waves. The most frequently used parameter, the percentage of normal slow waves, was first proposed by Chen (Chen and McCallum 1995; Chen et al. 1995a). It is defined as the percentage of time during which normal gastric slow waves (2–4 cpm in humans and 3.5–7.0 cpm in dogs) is detected from the time-frequency analysis of the EGG. This same parameter is used to provide feedback control of the strength of RGES in the subject method.

The first method of time-frequency analysis developed by Chen was called adaptive spectral analysis (Chen et al. 1990). It is based on an autoregressive moving average (ARMA) model and implemented using an adaptive ARMA filter. The parameters of the adaptive ARMA filter are adapted each time when a new sample is available using the least mean square (LMS) algorithm. The instantaneous frequency of the signal is computed from the filter parameters based on the ARMA model. This method has been refined and used for numerous years (Chen and McCallum 1995; Chen et al. 1995a; Chen et al. 1993; Lin and Chen 1996; Chen and McCallum 1991). It is adaptive, robust and relatively simple in computation.

Choi-William exponential distribution.

The second method for the time-frequency analysis of the EGG was the Choi-Williams exponential distribution (Lin and Chen 1994). This method was introduced by Choi and Williams (1989). It is a new distribution with an exponential-type kernel, which they called exponential distribution. This method was initially developed to solve the problem of cross-terms generated by the Wigner distribution. An optimal performance may be obtained for a particular application by a tradeoff between cross-term suppression and auto-term reduction. Experimental data with the EGG show that this method provides a good performance when the EGG has a high signal-to-noise ratio. The performance is not satisfactory when the EGG is corrupted with noises and interference.

Overcomplete signal representation.

Traditionally, a signal is represented using an expansion of a particular orthogonal basis, such as Fourier basis, discrete cosine basis and wavelet basis, and the number of expansion is chosen such that the representation is unique. This representation is called complete signal representation. In contrast to complete signal representation, overcomplete signal representation uses a higher number of bases than the number of frequency components of the signal. Most recently, the concept of overcomplete signal representation has been applied for the time frequency analysis of the gastric slow wave and two algorithms have been proposed for the optimization of the overcomplete signal representation. One algorithm is the fast algorithm of matching pursue and the other is based on an evolutionary program (Wang et al. 1998). In addition, the so-called minimum fuel model was utilized and a special neural network was developed for it to optimize overcomplete signal representation.

Selection of the time-frequency analysis method.

Selection of the time-frequency analysis method to be used in the RGES system is based on the following criteria: 1) reliability and robustness; 2) accuracy; and 3) feasibility. A comparison among various time-frequency analysis methods was previously made (Lin and Chen 1995). The adaptive spectral analysis method is probably the best for this RGES system. It is reliable and robust. Its accuracy has been validated in several different studies (Chen et al. 1993 80; Chen and McCallum 1991). It uses the least mean square (LMS) algorithm (simple in computation), which makes it very feasible to be incorporated into an implantable stimulator. Other methods, such as STFT, exponential distribution and WT, can be investigated in comparison with the adaptive spectral analysis method. The over-complete signal representation method is probably too complicated for an implantable device (Wang et al. 1998).

Adaptive Spectral analysis is based on the autoregressive moving average (ARMA) model. In this method, it is assumed that a signal $s_n$ (n: time instant) can be generated by exciting an ARMA process using a random time series, $n_n$. Mathematically, it can be written as follows:

$$S_n = -\sum_{k=1}^{p} a_k s_{n-k} + \sum_{k=1}^{q} c_k n_{n-k} + n_n$$

where $a_k$ (k=1, 2, . . . ,p) and $c_k$, (k=1,2, . . . q) are called the ARMA parameters. The power spectrum of the signal, $s_n$, can be calculated from these ARMA parameters.

Figure 14:
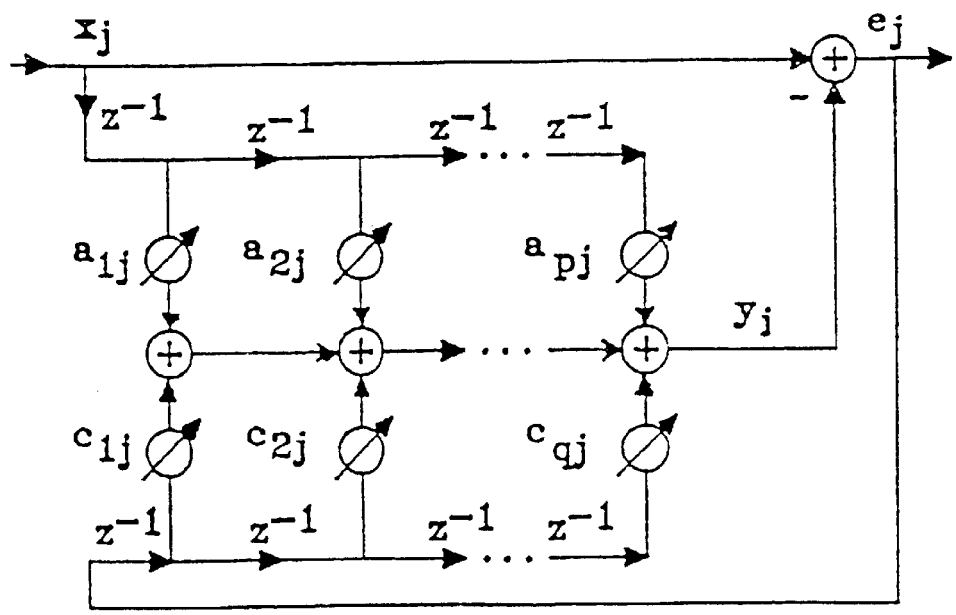
FIG. 14 details the structure of the adaptive ARMA filter.

To model a real signal $x_n$, one simply proceeds in the opposite direction. By constructing a so-called adaptive ARMA filter (see FIG. 14, $z^{-1}$ stands for one sample delay), the output signal, $y_n$, now can be made to approximate the input signal, $x_n$. It is expressed as:

$$y_n = \sum_{k=1}^{p} a_{k,n} x_{n-k} + \sum_{k=1}^{q} c_{k,n} e_{n-k}$$

where $a_{k,n}$ and $c_{k,n}$ are time-varying parameters and $e_n$ is the estimation error:

$$e_n = X_n - y_n$$

The ARMA parameters are initially set as zeros and iteratively adjusted by the least mean squares (LMS) algorithm, expressed as follows:

$$c_{k,n+1} = c_{k,n} + 2\mu_c e_n e_{n-k}, k = 1, 2, \ldots, q$$
$$a_{k,n+1} = a_{k,n} + 2\mu_a e_n e_{n-k}, k = 1, 2, \ldots, p$$

where step-sizes, $\mu_a$ and $\mu_c$, are small constants controlling the adaptation speed of the LMS algorithm (Chen et al. 1993). The algorithm states that the filter parameters at each successive time step, $a_{k,n+1}$ and $C_{k,n+1}$, are equal to their current values, $a_{k,n}$ and $c_{k,n}$, plus a modification term. The number of the filter parameters used is equal to q+p. The best value for q may be associated with specific applications. The value of p must be greater than or equal to the number of digitized points that span the longest rhythmic cycle of interest in a signal. For example, if the period of the rhythmic component of interest in a signal is 20 seconds (0.05 Hz or 3.0 cpm) and the sampling frequency is 2 Hz, the smallest value of p should be 40. This requirement of this large value is attributed to the nature of the LMS algorithm.

Once the adaptive filter converges, the power spectrum of the input signal $x_n$ can be calculated from the filter parameters. At any point in a time series, a power spectrum can be calculated instantaneously from the updated parameters of the model. Similarly, the power spectrum of the signal for any particular time interval can be calculated by averaging the filter parameters over that time interval.

Figure 15:
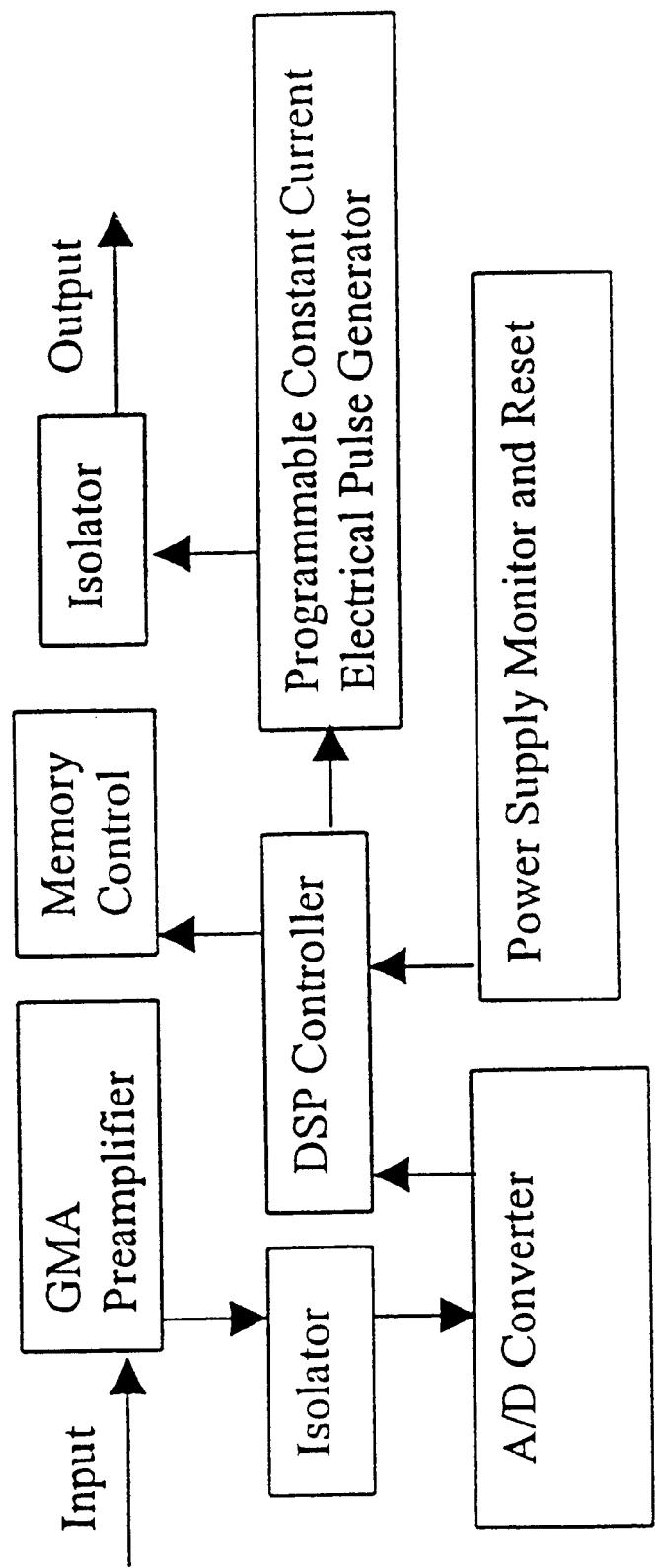
FIG. 15 is a block diagram of a portable stimulator.

The implementation of the RGES system in a portable device is shown in FIG. 15. It contains similar components as those shown in FIG. 13. A new element of the RGES stimulator is the addition of a DSP (digital signal processing) controller.

EXAMPLE III

Portable stimulators for gastric electrical stimulation are feasible and effective.

A portable electrical stimulator was previously developed (Chen et al. 1995b) and used in more than 20 patients (see FIG. 9). The stimulator uses fixed parameters and delivers stimulation pulses with a frequency of 3 cpm, pulse width of 300 ms and pulse amplitude of 4 mA (constant current mode). The constant current is guaranteed with a load in the range of 300–1000 W. The stimulator is operated by a 9-volt battery with an easy access for replacement. A female pin is available to connect the stimulator with the stimulation electrode wire. There is a manual switch for turning on or off the stimulator. This stimulator has been used in a clinical research study (McCallum et al. 1998) with no malfunction or adverse events reported.

EXAMPLE IV
Electrical Field Stimulation

This example illustrates the entrainment of gastric slow waves and the acceleration of gastric emptying using gastric electrical field stimulation. Two electrodes are placed on the serosa of the stomach. Unlike the bipolar or monopolar methods of the prior art, one electrode is placed in the proximal stomach and the other in the distal stomach. The proximal electrode has a positive polarity, and the distal one has a negative polarity. Electrical stimulation is performed via these two electrodes. The stimulation frequency is 10% higher than the natural frequency of the gastric slow waves. Instead of single pulses, a train of pulses with a frequency in the range of 1 to 50 Hz is used for each stimulus.

By placing the two stimulator electrodes in the gastric cardiac area close to the lower esophageal sphincter (LES), the methods can be used for the treatment of gastric esophageal reflux (by increasing the LES pressure) or achalasia (by relaxing the LES).

EXAMPLE V

Electrical Field Stimulation of the Vagus Nerve—gastric electrical stimulation affects vagal efferent activity in dogs.

Figure 11:
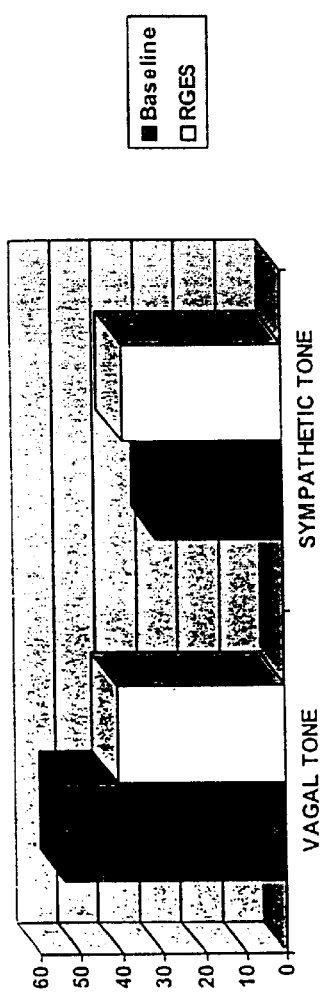
FIG. 11 illustrates the effect of RGES on vagal and sympathetic tone.

Evidence of an effect of gastric electrical stimulation on vagal activity is provided in this Example. These studies were performed in 5 healthy female hound dogs implanted with one pair of serosal electrodes on the greater curvature 2 cm above the pylorus. The experiment was performed in the fasting state after a complete recovery from surgery. The protocol consisted of 30-min baseline, 30-min stimulation and 30-min recovery. The stimulus was composed of a series of pulse trains. The pulse train was on for 2 seconds and off for 3 seconds. The pulse in each train had a frequency of 40 Hz, a pulse width of 200 $\mu$s and an amplitude of 4 mA. A significant increase in the ratio of sympathetic and vagal activities (assessed using the spectral analysis of the heart rate variability signal as described) was observed with RGES (0.93±0.49 with GRES in comparison with 0.67±0.49 (p<0.04) at baseline). This increase was attributed to an decrease in the percentage of vagal activity (40.6±9% vs. 54±12%, p=0.06) and an increase in the percentage of sympathetic activity (39±12% vs. 31±14%, p<0.05) (see FIG. 11)(Wang et al. 2000b)

In another experiment (Wang et al. 2000a), the effect of different stimulation frequencies on vagal efferent activity in 5 dogs was investigated using antegrade gastric electrical stimulation. It was found that stimulation at a physiological frequency enhanced vagal efferent activity, whereas stimulation at a tachygastrial frequency inhibited vagal efferent activity.

EXAMPLE VI
Placement of Electrodes

This example illustrates a method for the placement of electrodes in the gut without any surgical intervention. The prior art methods of electrode placement generally involve the implantation of electrodes on the serosa of the gut via open surgery or laparoscopic surgery. General anesthesia and hospital stay are necessary.

In this example, electrodes are placed via endoscopy without general anesthesia or hospital stay. First, the conscious patient is sedated and an endoscope is inserted into the stomach or small intestine via the mouth. This step is optional, and is for the purpose of observing the placement of the electrodes. Then, a sharp, long and small needle with a hole in the middle (the same needle used for the placement of percutaneous endoscopic gastrostomy tubes) is inserted into the stomach or small intestine. A teflon-isolated wire is then inserted into the stomach or small intestine via the hole of the needle under endoscopy. The teflon at the distal portion of the wire is peeled off so that the exposed portion of the wire serves as an electrode. There are barbs arranged circumferentially at the end tip of the wire. The needle is removed after the insertion of the wire. The wire is slowly pulled back until the barbs contact the mucosa and stop the wire from being further pulled out. The wire on the abdomen is attached to the abdominal skin and protected from infection. Various numbers of wires can be placed in this manner, without the need to hospitalize the patient. Therefore, the patient can be discharged after a few hours of recovery from sedation.

The monitoring and electrical stimulation of the colon can also be done, with the electrodes being placed in a similar manner but via colonoscopy.

Although preferred embodiments have been depicted and described in detail herein, it will be apparent to those skilled in the relevant art that various modifications, additions, substitutions and the like can be made without departing from the spirit of the invention and these are therefore considered to be within the scope of the invention as defined in the claims which follow.

REFERENCES

AACE/ACE Position Statement on the Prevention, diagnosis, and treatment of obesity. Endocrine Practice 4:297–330 (1998).

Abo, M, et al., Dig Dis Sci 45:129–135 (2000).

Akay, M., Ed., *Time frequency and wavelets in biomedical signal processing*. IEEE Press, New York (1995).

Alpert, M A and M W Hashimi, Am J Med Sci 306:117–123 (1993).

Asakawa, A, et al., Gastroenterology 116:1287–1292 (1999). Balsiger, B M, et al., Medical Clinics of North America 84 (2) :477–489 (2000).

Bandini, L G, et al., Am J Clin Nutr 52:421–425 (1990).

Bellahsene, B E, et al., Am J Physiol 262:G826–G834 (1992).

Benotti, P N and R A Forse, Am J Surg 169:361–367 (1995).

Bray, G A and F L Greenway, Endocr Rev 20(6):805–875 (1999).

Brolin, R E, et al., Ann Surg 215:387–395 (1992).

Chen, J D Z and Z Y Lin, Comp Biol Med 23:497–509 (1993).

Chen, J D Z and R W McCallum, Med Biol Eng Comput 29:339–350 (1991).

Chen, J D Z and R W McCallum, Am J Gastroenterol 88:1324–1336 (1993).

Chen, J D Z and R W McCallum, *Electrogastrography: principles and applications*. New York: Raven (1995).

Chen, J D Z, et al., Med Biol Eng Comput 27:57–63 (1989).

Chen, J D Z, et al., Med Biol Eng Comput 28:531–536 (1990).

Chen, J D Z, et al., IEEE Trans Biomed Eng 40:128–135 (1993).

Chen, J D Z, et al., Dig Dis 13:275–290 (1995a).

Chen, J D Z, et al., Proc 17th Intl Conf IEEE Eng Med Biol Soc, Canada (1995b).

Chen, J D Z, et al., IEEE-EMBC and CMBEC, Theme 7: Instrumentation, pp. 1691–1692 (1995c).

Chen, J D Z, et al., J Gastro Hepato 13(Suppl.):5232–5236 (1998).

Choi, H-I and W J Williams, IEEE Trans ASSP 37:862–871 (1989).

Cohen, L, in *Time-Frequency Signal Analysis—Methods and Applications*, Boashash, B, Ed., Melbourne, Longman-Cheshire, pp 3–42 (1992).

Colditz, G A, Am J Clin Nutr 55(Suppl 2):503S–507S (1992).
Consensus Development Conference Panel, Annals of Internal Medicine 15:956–961 (1991).
Despres, J P, Nutrition 9:452–459 (1993).
Doldi, S B, et al., Obesity Surgery 10(2):171–173 (2000).
Douglas, N J, Eur J Clin Invest 25:285–290 (1995).
Duggan, J P and D A Booth, Science 231:609–611 (1986).
Eagon, J C and K A Kelly, Am J Physiol 265:G767–G774 (1993).
Enzi, G, PharmacoEconom 5(Suppl 1):54–57 (1994).
Enzi, G, et al., J Int Med Res 4:305–318 (1976).
Flegal, K M, et al., Int J Obse Relat Metab Disord 22:39–47 (1998).
Frederich, R C, et al., Nat Med 1:1311–1314 (1995).
Fried, M, et al., Hepatogastroenterology 44:582–587 (1997).
Gortmaker, S L, et al., N Engl J Med 329:1008–1012 (1993).
Greenway, F L, Am J Clin Nutr 55(Suppl 1):203S–205S (1992).
Grossman, A and J Morlet, SIAM J Math Anal 15:723–736 (1984).
Hocking, M P, et al., Gastroenterol 103:1811–1816 (1992).
House Committee on Small Business. Deception and Fraud in the Diet Industry: Hearing Before the Subcommittee on Regulation, Business Opportunities, and Energy, 101st Congress, 2nd Session. Washington, DC: Government Printing Office, 101–150 (1990).
Hvizdos, K M and A Markham, Drugs 58(4):743–760 (1999).
Institute of Medicine Food and Nutrition Board Committee to Develop Criteria for Evaluating the Outcomes of Approaches to Prevent and Treat Obesity. In: *Weighing the Options: Criteria for Evaluating Weight-Management Programs*. Thomas, P R, Ed., Washington DC: National Academy Press (1995).
Kissebah, A H, et al., Med Clin North Am 73:111–138 (1989).
Klein, S, Clinical Perspectives in Gastroenterology 3:232–236 (2000).
Kuczmarski, R J, et al., JAMA 272:205–211 (1994).
Kuczmarski, R J, et al., Obes Res 5:542–548 (1997).
Lasagna, L, *Phenylpropanolamine: a Review*. New York: John Wiley & Sons (1988).
Le Riche, W H and A Csima, Can Med Assoc J 97:1016–1020 (1967).
Lin, Z Y and J Chen, IEEE Trans Biomed Eng 41:267–275 (1994).
Lin, Z Y and J D Z Chen, Med Biol Eng Comput 33:596–604 (1995).
Lin, Z Y and J D Z Chen, Crit Rev Biomed Eng 24:1–72 (1996).
Lin, Z Y, et al., Am J Physiol 274(1 Pt 1):G186–191 (1998).
Lin, X M, et al., Gastroenterology 116:A970 (1999).
Lin, X M, et al., Dig Dis Sci 45:652–656 (2000a).
Lin, X M, et al., Ann of Biomedical Engineering 28:582–587 (2000b).
Lu, C L, et al., Dig Dis Sci 44:857–861 (1999).
Martin, L F, et al., South Med J 88:895–902 (1995).
McCallum, R W, et al., Gastroenterol 114:456–461 (1998).
Miedema, B W, et al., Surg 111:143–150 (1992).
Mintchev et al., Gut 43(5):607–611 (1998).
Mintchev et al., Journal of Medical Engineering & Technology 23(1):5–9 (1999).
Mintchev et al., Gastroenterology 118(2):258–263 (2000).
Moran, T H and P R McHugh, Am J Physiol 242:R491–R497 (1982).
Morley, J E, Endocr Rev 8:256–287 (1987).
Nakajima, T, et al., Circulation 71:481–486 (1985).
Namnoum, A B, Female Patient 18:33–44 (1993).
National Institutes of Health Consensus Development Panel on the Health Implications of Obesity. Ann Intern Med 103(6 Pt 2):1073–1077 (1985).
Nightengale, M L, et al., May Clin Proc 66:773–782 (1991).
Phillips, R J and T L Powley, Am J Physiol 271:R766–R779 (1996).
Qian, L W, et al., Am J Physiol (Gastrointest Liver Physiol 39) 276:G387–392 (1999).
Rodet, X, Comput Music J 8:part 3 (1985).
Sagar, P M, Br J Surg 82:732–739 (1995).
Scopinaro, N, et al., Int J Obes 5:421–429 (1981).
Scopinaro, N, et al., Surgery 119:261–268 (1996).
Sheldon, R J, et al., Regul Pept 28:137–141 (1990).
Smith, I G, "Long-term weight loss with sibutramine (MERIDIA®), a once-daily serotonin and norepinephrine reuptake inhibitor." Abstract presented at the annual conference of the North American Association for the Study of Obesity; Cancun, Mexico (November 1997).
Sobal, J, et al., Psychol Bull 105:260–275 (1989).
Stunkard, A J, Am J Med 100:230–236 (1996).
Sugerman, H J, et al., Am J Clin Nutr 55(Suppl 2):560S–566S (1992).
Telander, R L, et al., Gastroenterology 75:495–501 (1978).
Thompson, P D, N Engl J Med 337:1772 (1997).
Tougas, G, et al., Am J Gastroenterology 95:1456–1462 (2000).
Troiano, R P, et al. Arch Pediatr Adolesc Med 149:1085–1091 (1995).
Van Itallie, T B, Ann Intern Med 103:983–988 (1985).
Ville, J, Cables et Transmission 2A:61–74 (1948).
Wang, Z S, et al., Ann Biomed Eng 26:859–869 (1998).
Wang, Z S, et al., Gastroenterology 118:A669 (2000a).
Wang, Z S, et al., Gastroenterology 118:A1204 (2000b).
Wigner, E P, Phys Rev 40:749–759 (1932).
Wolf, A M and G A Colditz, Obes Res 6:97–106 (1998).
Wright, R A, et al., Gastroenterology 84:747–751 (1983).
Yamada, T, et al., Eds., *Textbook of Gastroenterology*. Philadelphia: J. B. Lippincott Company (1995).
You, C H and W Y Chey, Gastroenterology 86:1460–1468 (1985).

What is claimed is:

1. A method of regulating gastrointestinal action in a subject, the method comprising:

determining an optimum level of total gastrointestinal action in a subject, the total gastrointestinal action including naturally occurring gastrointestinal action and non-naturally occurring gastrointestinal action;

positioning a stimulatory electrode relative to the subject so that the stimulatory electrode can generate non-naturally occurring gastrointestinal action;

positioning a sensor relative to the subject so that the sensor senses the level of total gastrointestinal action, the sensor being operatively connected to the stimulatory electrode;

periodically detecting the level of total gastrointestinal action with the sensor; and periodically generating non-naturally occurring gastrointestinal action with the stimulatory electrode when the detected level of total gastrointestinal action differs from the optimum level until the detected level of total gastrointestinal action substantially equals the optimum level.

2. The method of claim 1 wherein the gastrointestinal action is gastrointestinal electrical activity.

3. The method of claim 1 wherein the gastrointestinal action is gastrointestinal contractile activity.

4. The method of claim 3 wherein the contractile activity is stomach contractile activity.

5. The method of claim 1 wherein the gastrointestinal action is gastrointestinal motility.

6. The method of claim 1 wherein the gastrointestinal action is gastric emptying.

7. The method of claim 1 wherein the gastrointestinal action is gastrointestinal pressure.

8. The method of claim 1 wherein the gastrointestinal action is vagal activity.

9. The method of claim 1 wherein the gastrointestinal action is gastrointestinal impedence.

10. The method of claim 1 wherein the gastrointestinal action is afferent nerve activity.

11. A method for reducing weight in a subject having a stomach, the method comprising:

determining an optimum level of total stomach electrical activity in a subject which reduces weight in the subject, the total stomach electrical activity including naturally occurring stomach electrical activity and non-naturally occurring stomach electrical activity;

positioning a stimulatory electrode relative to the subject so that the stimulatory electrode can generate non-naturally occurring stomach electrical activity;

positioning an electrical activity sensor relative to the subject so that the electrical activity sensor senses the level of total stomach electrical activity, the electrical activity sensor being operatively connected to the stimulatory electrode;

periodically detecting the level of total stomach electrical activity with the electrical activity sensor; and periodically generating non-naturally occurring stomach electrical activity with the stimulatory electrode when the detected level of total stomach electrical activity differs from the optimum level until the detected level of total stomach electrical activity substantially equals the optimum level.

* * * * *